United States Patent [19]
Sanderson et al.

[11] Patent Number: 6,017,934
[45] Date of Patent: Jan. 25, 2000

[54] THROMBIN INHIBITORS

[75] Inventors: Philip E. Sanderson, Philadelphia; Terry A. Lyle, Lederach; Craig Coburn, Skippack, all of Pa.

[73] Assignee: Merck & Co., Inc., Rahway, N.J.

[21] Appl. No.: 09/009,616

[22] Filed: Jan. 20, 1998

Related U.S. Application Data

[60] Provisional application No. 60/036,149, Jan. 22, 1997.

[51] Int. Cl.[7] .................. C07D 213/02; A61K 31/445
[52] U.S. Cl. ................ 514/332; 514/346; 546/255; 546/292
[58] Field of Search ................ 546/255, 292; 514/332, 349, 346

[56] References Cited

U.S. PATENT DOCUMENTS

| | | | |
|---|---|---|---|
| 5,260,307 | 11/1993 | Ackermann et al. | 514/323 |
| 5,405,854 | 4/1995 | Ackermann et al. | 514/315 |
| 5,510,369 | 4/1996 | Lumma et al. | 514/422 |

FOREIGN PATENT DOCUMENTS

| | | |
|---|---|---|
| 509 769 A2 | 10/1992 | European Pat. Off. . |
| WO 94/25051 | 11/1994 | WIPO . |
| WO 96/11697 | 4/1996 | WIPO . |
| WO 96/31504 | 10/1996 | WIPO . |
| WO 96/32110 | 10/1996 | WIPO . |
| WO 97/01338 | 1/1997 | WIPO . |

OTHER PUBLICATIONS

Bernstein et al., J. Med. Chem., "Nonpeptidic Inhibitors of Human Leukocyte Elastase. 3.1 Design, Synthesis, X–ray Crystallographic Analysis, . . . ", vol. 37, pp. 3313–3326 (1994).

Edwards et al., J. Am. Chem. Soc., "Design, Synthesis, and Kinetic Evaluation of a Unique Class of Elastase Inhibitors, . . . ", vol. 114(5), pp. 1854–1863 (1992).

Brown et al., J. Med. Chem., "Design of Orally Active, Non–Peptidic Inhibitors of Human Leukocyte Elastase", vol. 37(9), pp. 1259–1261 (1994).

*Primary Examiner*—Zinna Northington Davis
*Attorney, Agent, or Firm*—Richard S. Parr; Melvin Winokur

[57] ABSTRACT

A compound which inhibits human thrombin and where has the structure

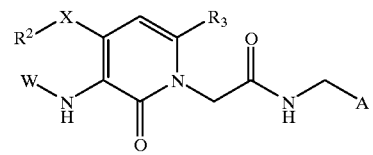

such as

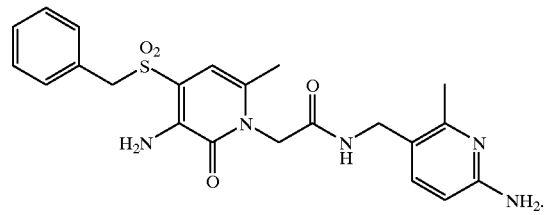

12 Claims, No Drawings

THROMBIN INHIBITORS

This application claims as priority provisional application No. 60/036,149 filed Jan. 22, 1997.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.* (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoimino-methyl)amino]butyl]-1-[N-(2-naphthalenylsulfonyl)-L-phenylalanyl]-L-prolinamide.

WO 94/29336 describes compounds which are useful as thrombin inhibitors.

WO 96/18644 describes heterocyclic derivatives as thrombin inhibitors.

SUMMARY OF THE INVENTION

The invention relates to compounds of the formula:

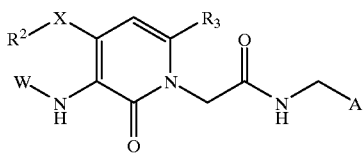

wherein
W is
  hydrogen,
  $R^1$—,
  $R^1OC(O)$—,
  $R^1C(O)$—,
  $R^1SO_2$—,
  $(R^1)_m(CH_2)_nNHqC(O)$—,
    where n is 0–4, m is 1 or 2, wherein $R^1$ is same or different, and q is 0 or 1, with the proviso that where n is 1–4, q is 1 and m is 1, and where n is 0, m is 1 or 2, and q is 0 or 1, and where n is 0, m is 2 and q is 0;
$R^1$ is
  $R^{17}(CH_2)_t$—, where t is 0–4;
  $(R^{17})(OR^{17})CH(CH_2)_p$—, where p is 1–4,
  $(R^{17})_2CH(CH_2)_r$—, where r is 0–4 and each $R^{17}$ can be the same or different, and wherein $(R^{17})_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S,
  $R^{17}O(CH_2)_p$—, wherein p is 1–4;
$R^2$, $R^{14}$ and $R^{17}$ are independently selected from
  -phenyl, unsubstituted or substituted with one or more of
    $C_{1-4}$ alkyl,
    $C_{1-4}$ alkoxy,
    halogen,
    hydroxy,
    COOH, or
    $CONH_2$,
  naphthyl,
  biphenyl,
  a 5- to 7-membered mono- or a 9- to 10-membered bicyclic heterocyclic ring which can be saturated or unsaturated, and which contains from one to four heteroatoms selected from the group consisting of N, O and S,
  —$C_{1-7}$ alkyl, unsubstituted or substituted with one or more of
    hydroxy,
    COOH,
    amino,
    aryl,
    $C_{3-7}$ cycloalkyl,
    heteroaryl, or
    heterocycloalkyl,
  —$CF_3$
  $C_{3-7}$ cycloalkyl,
  $C_{7-12}$ bicyclic alkyl, or
  $C_{10-16}$ tricyclic alkyl;
X is
  $CF_2$,
  $CR^{15},R^{16}$
    wherein $R^{15}$ and $R^{16}$ are independently
    hydrogen,
    $C_{3-7}$ cycloalkyl,
    $C_{1-4}$ alkyl unsubstituted or substituted with one or more of
      hydroxy,
      COOH,
      amino,
      aryl,
      heteroaryl, or
      heterocycloalkyl,
    aryl,
    heteroaryl,
    heterocycloalkyl, or
    $R^{15}$ and $R^{16}$ are joined to form a four to seven membered cycloalkyl ring unsubstituted or substituted with hydroxy, amino or aryl, or
  $S(O)_r$, where r is 0–2;
$R^3$ is
  hydrogen,
  $C_{1-4}$ alkyl,
  $C_{3-7}$ cycloalkyl, or
  trifluoromethyl;

A is chosen from one of the following radicals:

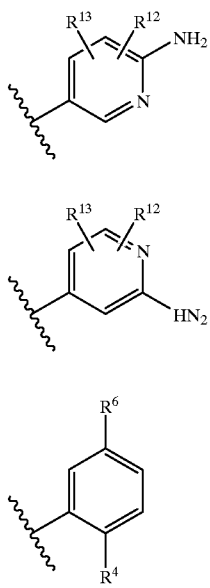

with the proviso that when A is radical IV, $R^2$—X is not $C_{1-4}$ alkyl, $C_{3-7}$ cycloalkyl, or trifluoromethyl;

$R^4$ is
hydrogen,
$C_{1-4}$ alkyl,
$C_{1-4}$ alkoxy,
halogen,
—$OCH_2CF_3$,
—COOH,
—OH,
—$COOR^6$, where $R^6$ is $C_{1-4}$alkyl,
—$CONR^7R^8$, where $R^7$ and $R^8$ are independently hydrogen or $C_{1-4}$alkyl,
—$(CH_2)_{1-4}OH$,
—$CH_2NHC(O)CH_3$,
—$CH_2NHC(O)CF_3$,
—$CH_2NHSO_2CH_3$,
—$SO_2NH_2$,
—$(CH_2)_{1-4}SO_2NR^7R^8$,
—$(CH_2)_{1-4}SO_2R^6$,
a 5- to 7-membered mono- or a 9- to 10-membered bicyclic heterocyclic ring which can be saturated or unsaturated, and which contains from one to four heteroatoms selected from the group consisting of N, O and S,
—$ZCH_2CO_2H$,
—$ZCH_2CO_2CH_3$,
—$ZCH_2R^{14}$,
—$ZCH_2CO_2(CH_2)_{1-3}CH_3$,
—$Z(CHR^9)_{1-3}C(O)NR^{10}R^{11}$,
wherein
$R^9$ is H or $C_{1-4}$ alkyl,
$R^{10}$ and $R^{11}$ are independently
hydrogen,
$C_{3-7}$ cycloalkyl,
aryl,
heteroaryl,
heterocycloalkyl,
$C_{1-4}$ alkyl unsubstituted or substituted with one or more of hydroxy,
COOH,
amino,
aryl,
heteroaryl, or
heterocycloalkyl, or
$R^{10}$ and $R^{11}$ are joined to form a four to seven membered cycloalkyl ring unsubstituted or substituted with hydroxy, amino or aryl,
wherein Z is O, S or $CH_2$;
$R^5$ is
hydrogen,
halogen,
$C_{1-4}$ alkyl,
$C_{1-4}$ alkoxy,
CN, or
$CO_2NH_2$; and
$R^{12}$ and $R^{13}$ are independently
hydrogen,
$C_{1-4}$ linear or branched alkyl or alkoxy,
$C_{3-7}$ cycloalkyl,
halogen, or
trifluoromethyl;
and pharmaceutically acceptable salts thereof.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating atrial fibrillation, deep venous thrombosis, pulmonary embolism, cardiac thromoembolism and associated stroke in patients with atrial fibrillation, mechanical heart valves, or recent myocardial infarction with decreased left ventricular function, disseminated intravascular coagulation, ocular build up of fibrin, unstable angina, refractory angina, transient ischemic attacks, thrombotic stroke, embolic stroke, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

A class of these compounds is

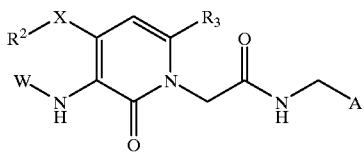

wherein
W is
 hydrogen,
 —$C_{1-4}$ alkyl,
 —$C_{3-7}$cycloalkyl,
 —$SO_2C_{1-7}$ alkyl, or
 —$(CH_2)_n$COOH, where n is 1–4;
$R^2$ is
 —$C_{1-7}$ alkyl
 —$(CH_2)_u$—$C_{3-7}$cycloalkyl, wherein u is 0, 1, or 2,
 —$(CH_2)_u$-phenyl, wherein phenyl is unsubstituted or substituted with one or more of the moieties selected from the group consisting of
  $C_{1-4}$ alkyl,
  $C_{1-4}$ alkoxy,
  halogen,
  hydroxy,
  COOH, or
  $CONH_2$
  wherein u is 0, 1, or 2,
 -2-thienyl, or
 -3-thienyl;
X is
 —S—, —$SO_2$—, or $CH_2$;
$R^3$ is
 $C_{1-4}$ linear alkyl;
A is chosen from one of the following radicals:

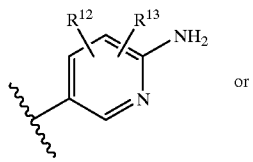  II

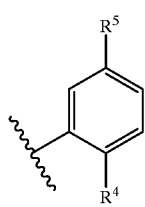  IV with the proviso that when A is radical IV, $R^2$-X- is not $C_{1-4}$ alkyl, and pharmaceutically acceptable salts thereof.

A group of this class of compounds is

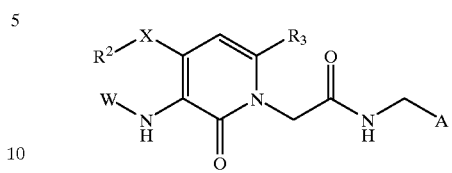

wherein
W is
 hydrogen,
 —$SO_2CH_3$, or
 —$CH_3$,
 —$CH_2COOH$;
$R^2$ is
 —$CH_3$,
 —$(CH_2)_u$—$C_{3-6}$cycloalkyl, wherein u is 0 or 1;
 —$(CH_2)_u$-phenyl, wherein u is 0 or 1,
 —$CH_2C(CH_3)_3$,
 —$CH(CH_3)_2$,
 -phenyl-$CH_3$,
 -2-thienyl, or
 -3-thienyl;
X is
 —S—, —$SO_2$—, or $CH_2$;
$R^3$ is
 —$CH_3$;
A is chosen from one of the following radicals:

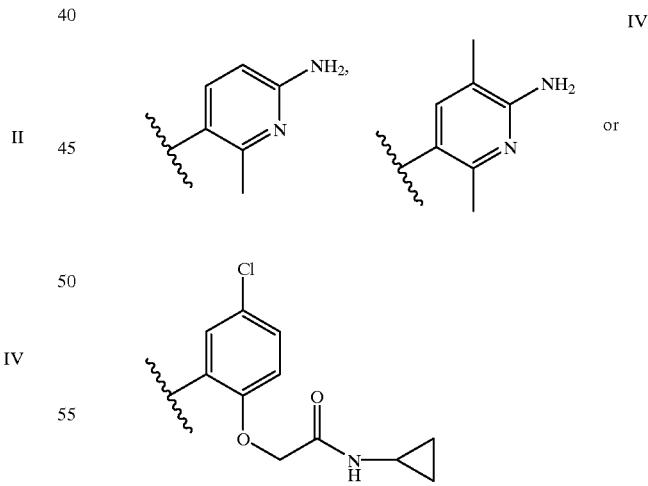

with the proviso that when A is radical IV, $R^2$-X- is not $C_{1-4}$ alkyl, and pharmaceutically acceptable salts thereof.

Specific embodiments of this group are

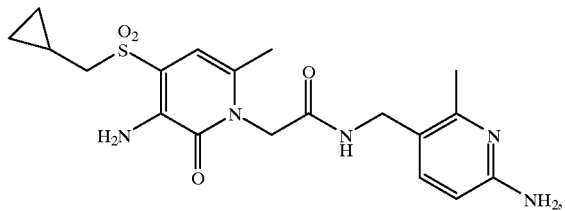
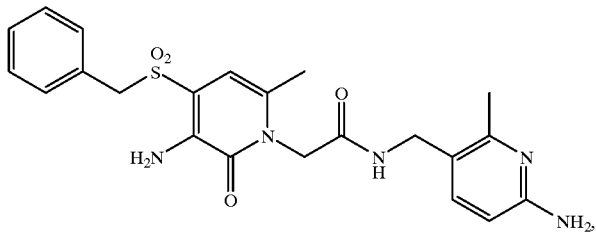
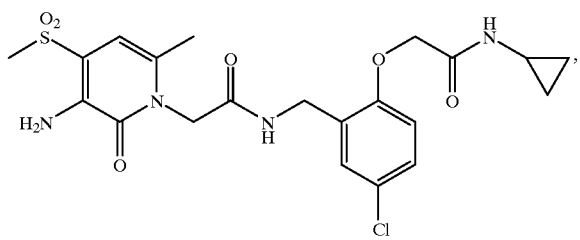
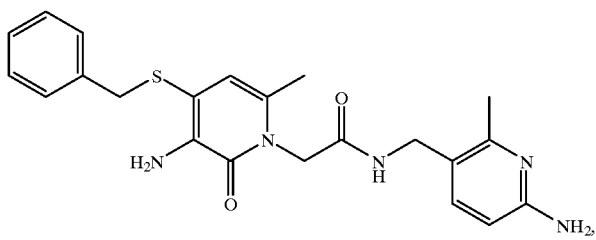
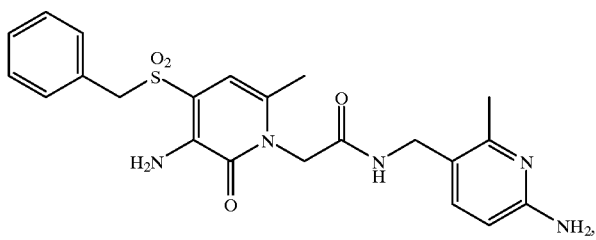
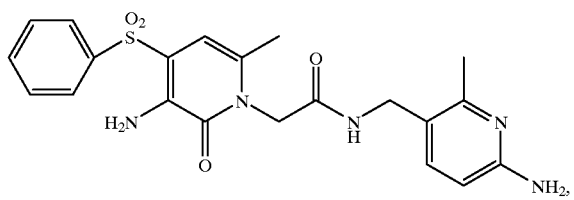
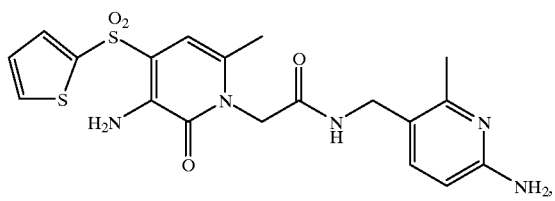

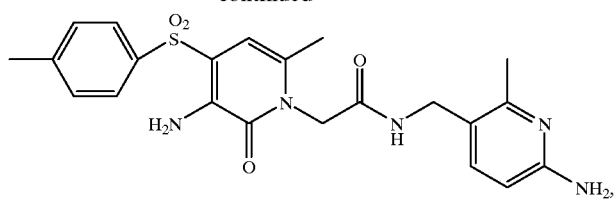
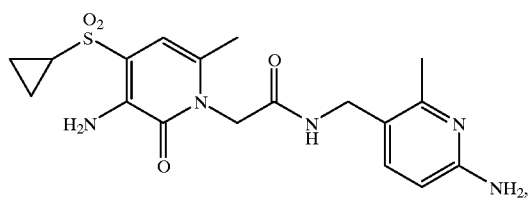
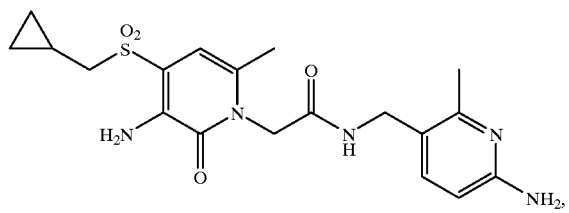
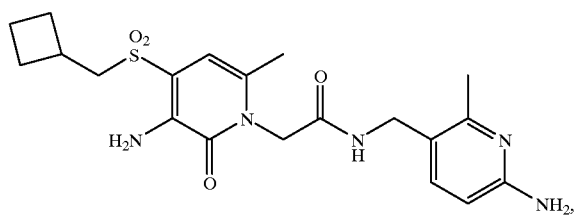
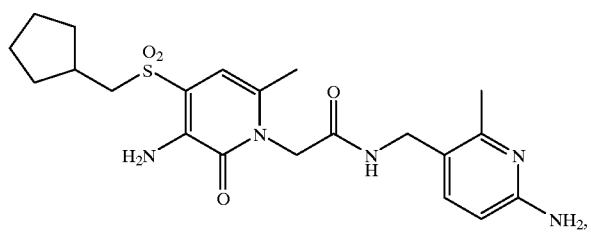
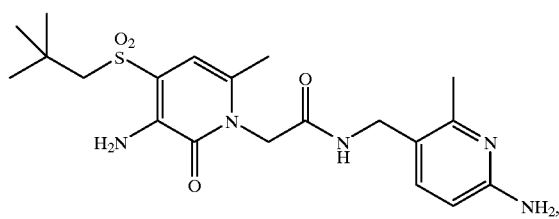
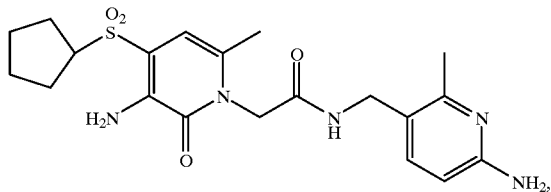
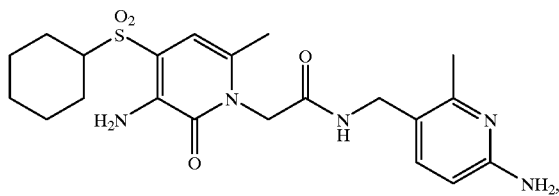

11
-continued
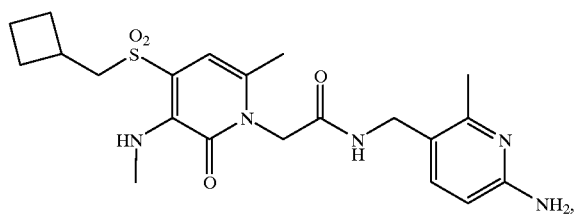
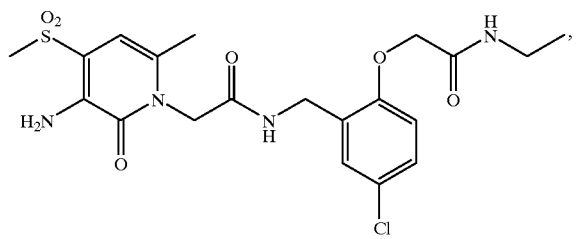
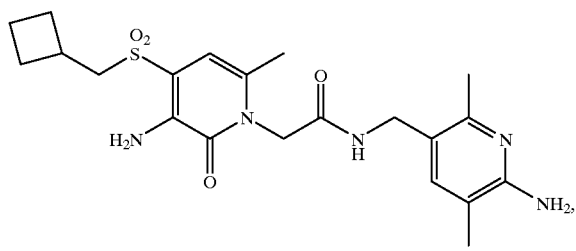
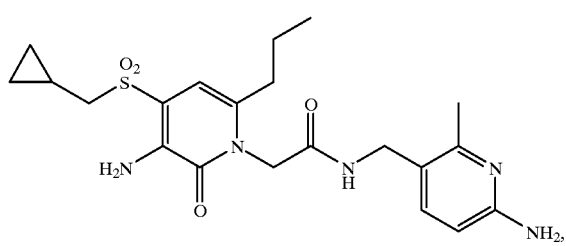
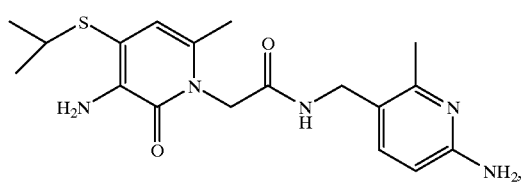
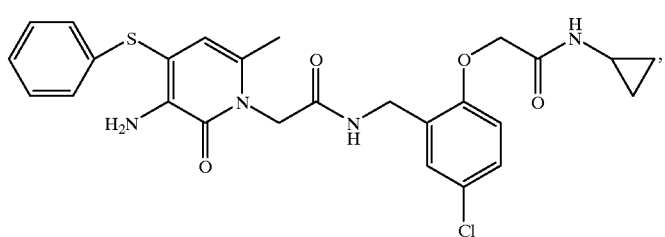
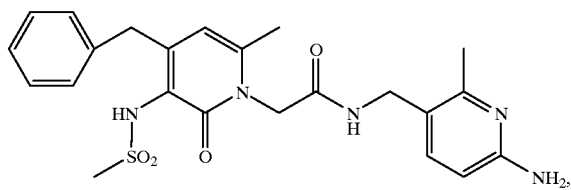
and -continued

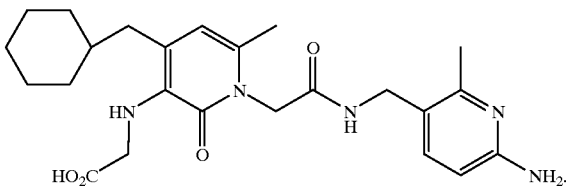

Compounds of the present invention, which are thrombin inhibitors, are useful in anticoagulant therapy. Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinlypyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.001 mg per kg of body weight per day (mg/kg/day) to about 100 mg/kg/day and preferably 0.01–100 mg/kg/day and most preferably 0.1–20 mg/kg/day. Intravenously, the most preferred doses will range from about 0.001 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 1 and 500 mg, e.g. 1, 10, 100, 200, 300, 400 or 500 mg. Typically, a patient in need of thrombin inhibitor compound, depending on weight and metabolism of the patient, would be administered between about 20 and 500 mg active compound per day. For a patient requiring 500 mg per day, two tablets containing 125 mg of active compound can be administered in the morning and two tablets containing 125 mg of active compound can again be administered in the evening. For a patient requiring 200 mg per day, one tablet containing 100 mg of active compound can be administered in the morning and one tablet containing 100 mg of active compound can again be administered in the evening. For patient requiring 10 mg per day, one tablet containing 5 mg of active compound can be administered in the morning and one tablet containing 5 mg of active compound can again be administered in the evening.

An i.v. formulation can be administered to patients requiring parenteral administration, such as hospitalized patients who are fasted (e.g. perioperative patients) and certain patients with indwelling catheters. For example, an i.v. formulation having 100 mg/ml active ingredient, at pH 4, could be administered twice a day at a dose of 0.5 ml/kg.

The compounds are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds can also be co-administered with suitable anti-coagulation agents or thrombolytic agents such as plasminogen activators or streptokinase to achieve synergistic effects in the treatment of various ascular pathologies. For example, the compounds enhance the efficiency of tissue plasminogen activator-mediated thrombolytic reperfusion. The compounds may be administered first following thrombus formation, and tissue plasminogen activator or other plasminogen activator is administered thereafter. They may also be combined with heparin, aspirin, or warfarin.

Compounds of the invention are shown in the table below. These compounds inhibit thrombin with the following potency according to in vitro measurements:

| Structure | trombin Ki (nM) |
|---|---|
| | ** |
| | ** |
| | * |

\* > 10
\*\* < 10

In vitro Assay for Determing Proteinase Inhibition

Assays of human a-thrombin and human trypsin were performed at 25° C. in 0.05 M TRIS buffer pH 7.4, 0.15 M NaCl, 0.1% PEG. Trypsin assays also contained 1 mM $CaCl_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin ($K_m$=125 $\mu$M) and human trypsin ($K_m$=59 $\mu$M). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m$=27 $\mu$M) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration $\leq 0.5$ $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where $[S]$, $[I]$, and e respectively represent the total concentrations, of substrate, inhibitor and enzyme), the equilibrium constant ($K_i$) for dissociation of the inhibitor from the enzyme can be obtained from the dependence of $V_o/V_i$ on $[I]$ shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Some abbreviations that may appear in this application are as follows.

| Designation | |
|---|---|
| BOC (Boc) | t-butyloxycarbonyl |
| HBT(HOBT or HOBt) | 1-hydroxybenzotriazole hydrate |
| BBC reagent | benzotriazolyloxy-bis(pyrrolidino)-carbonium hexafluorophosphate |
| PyClU | 1,1,3,3-bis(tetramethylene)-chlorouronium hexafluorophosphate |
| EDC | 1-ethyl-3-(3-dimethylaminopropyl) carbodiimide hydrochloride |
| (BOC)$_2$O | di-t-butyl dicarbonate |
| DMF | dimethylformamide |
| Et$_3$N or TEA | triethylamine |
| EtOAc | ethyl acetate |
| TFA | trifluoroacetic acid |
| DMAP | dimethylaminopyridine |
| DME | dimethoxyethane |
| BH$_3$-THF | Borane-tetrahydrofuran complex |
| D-Phe(3,4-Cl$_2$) | D-3,4-Dichlorophenylalanine |
| D-3,3-dicha | D-3,3-Dicyclohexylalanine |
| Pro | Proline |
| Arg | Arginine |
| Gly | Glycine |
| D-3,3,-diphe | D-3,3-Diphenylalanine |
| LAH | lithium aluminum hydroxide |
| Cy | cyclohexyl |
| POCl$_3$ | phosphorous oxychloride |
| MeCN | acetonitrile |
| BnEt$_3$N$^+$Cl$^-$ | benzyl triethyl ammonium chloride |
| NaH | sodium hydride |
| DMF | dimethylformamide |
| BrCH$_2$COO$^t$Bu | tert butyl bromoacetate |
| EtOH | ethyl alcohol |
| Pd(C) | palladium on activated carbon catalyst |

-continued

| Designation | |
|---|---|
| CF$_3$COOH | trifluoroacetic acid |
| DCM | dichloromethane |
| DIPEA | diisopropylethylamine |

The compounds of the present invention may have chiral centers and occur as racemates, racemic mixtures and as individual diastereomers, or enantiomers with all isomeric forms being included in the present invention.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like. The term "alkenyl" means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like. The term "alkynyl" means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like. Cycloalkyl means a cyclic, saturated ring containing 3 to 8 carbon atoms, e.g., cyclopropyl, cyclohexyl, etc. Halogen means chloro, bromo, fluoro or iodo. The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen-substituted derivatives thereof.

The pharmaceutically-acceptable salts of the compounds of the invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Unless otherwise stated, all NMR determinations were made using 400 MHz field strength.

The compounds of the present invention, where X is S(O)ᵣ, may be prepared using METHODS 1–5:

METHOD 1 (as exemplified by Example II)

Starting 2,4-dihydroxy-3-nitropyridine is reacted with a dehydrating chloride source, for example phosphorous oxychloride, in Step A to give the 4-chloropyridine. This is reacted in Step B with a thiol in the presence of a base such as triethylamine, and is then alkylated in Step C with an acetate equivalent such as t-butylbromoacetate. The ester may be deprotected by a strong acid such as TFA in Step D and the resulting carboxylic acid coupled in Step E with the appropriate amine, in this case cyclopropyl-(2-aminomethyl-4-chlorophenoxy)-acetamide (a method for the preparation of this class of amines is shown below) and the nitro group reduced in Step F by a reducing agent such as stannous chloride to give the final product.

Method for Making Ethyl-(2-aminomethyl-4-chlorophenoxy)-acetate

4-Chlorosalicaldehyde is condensed with hydroxylamine hydrochloride in ethanolic aqueous sodium carbonate solution in Step A. The oxime is reduced by hydrogenation over a catalyst such as rhodium and the amine is protected as its BOC derivative under standard conditions. The phenol is alkylated in Step D with an acetate equivalent such as ethyl bromoacetate and the resulting ester is hydrolysed with lithium hydroxide. The product carboxylic acid is coupled to an amine such as ethylamine or cyclopropylamine in Step F, and the BOC group is removed by strong acid such as TFA in Step G.

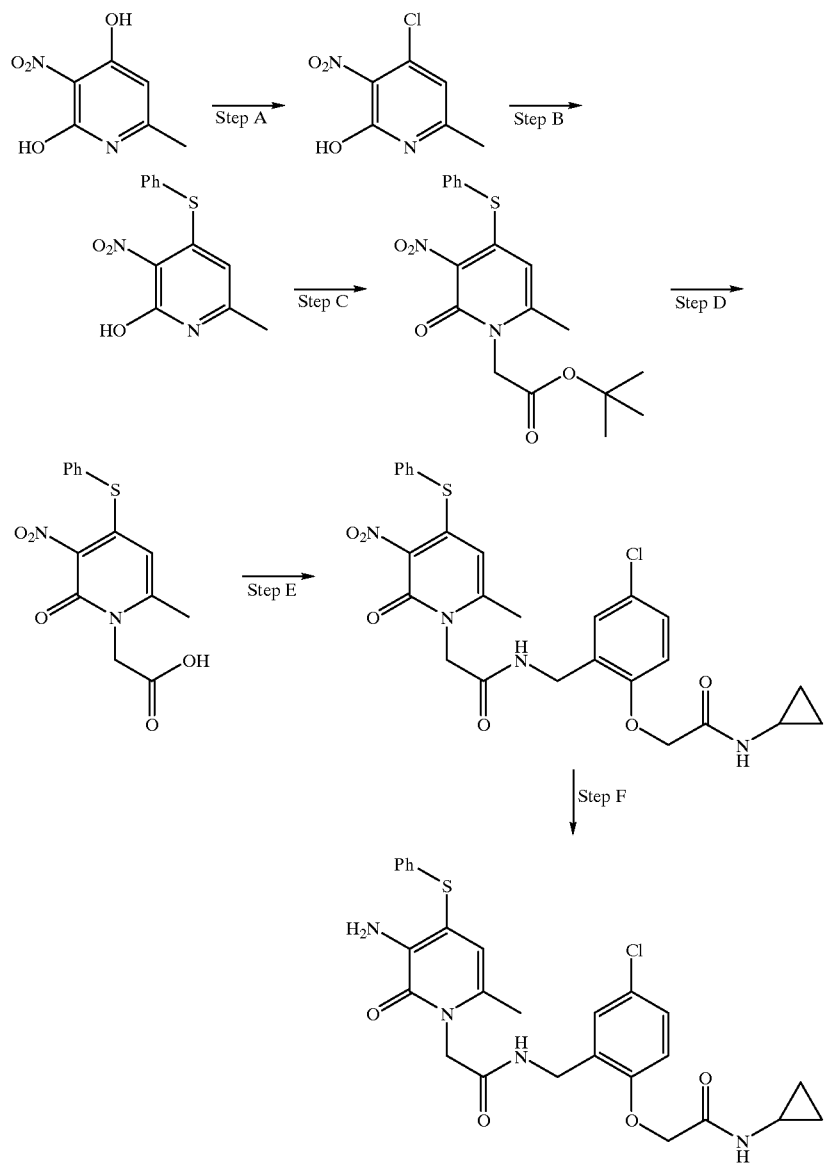

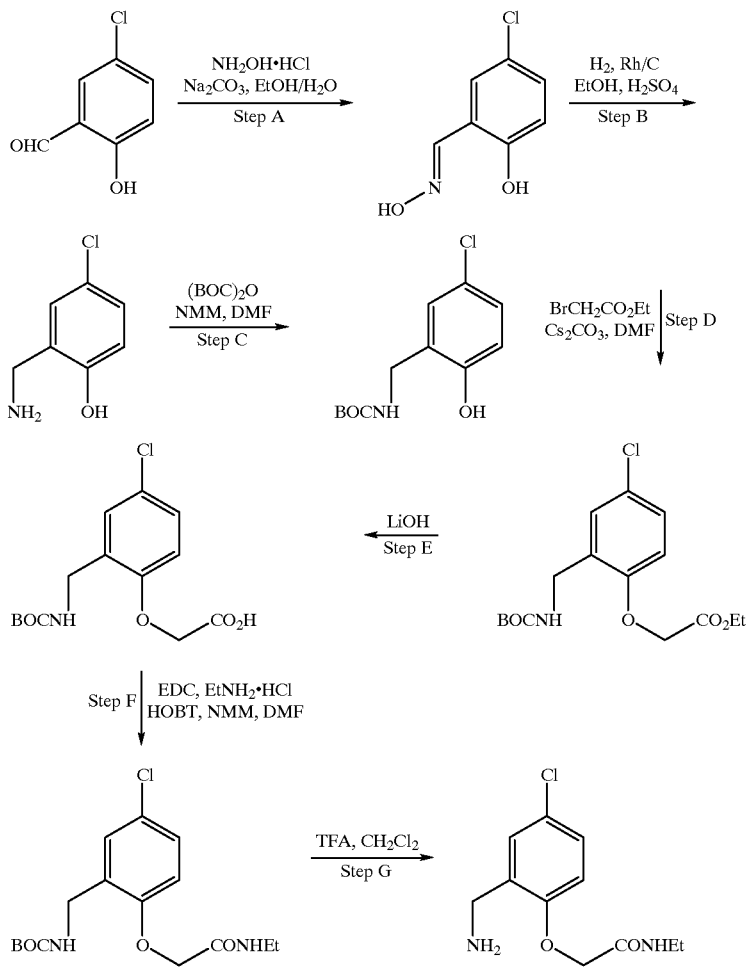

Modifications of this method will allow different $R^4$ and $R^5$ groups contemplated by the scope of the broad claim below to be present by the use of an appropriate reagent or appropriately substituted starting material in the indicated synthetic step. For example, appropriate choice of the amine in Step F will allow different values of $R^{10}$ and $R^{11}$ to be achieved. Obvious variations and modifications of the method to produce similar and obvious variants thereof, will be apparent to one skilled in the art.

Step A: 4-Chlorosalicaldehyde Oxime

A solution of hydroxylamine hydrochloride (16.7 g, 0.24 mol) and sodium carbonate (12.7 g, 0.12 mol) in water (120 ml) was added to a stirred solution of 4-chlorosalicaldehyde (25.0 g, 0.16 mol) in ethanol (160 ml) and the resulting solution was heated to reflux. After 1 h the reaction was cooled, water (320 ml) was added and the resulting crystalline precipitate was isolated by filtration. A second crop was similarly collected and the combined solids were dried to give the title compound:

$^1$H NMR (CDCl$_3$) d 6.92 (d, J=8.8 Hz, 1 H), 7.15 (d, J=2.6 Hz, 1H), 7.23 (dd, J=2.6 and 8.8 Hz, 1H), 7.26 (s, 1H), 8.16 (s, 1H), 9.71 (s, 1H).

Step B: 2-Hydroxy-5-Chlorobenzylamine

A mixture of 4-chlorosalicaldehyde oxime (10 g, 58.3 mmol) and 5% Rh/C (2.0 g) in ethanol (100 ml) containing concentrated sulfuric acid (10 ml) was shaken in a Parr apparatus under H$_2$ (60 psi) for 24 h. Water (100 ml) was added and the mixture was filtered through celite. The filtrate was concentrated until the product had crystallized out of solution. The solid was collected by filtration and the filtrate was further concentrated, adding water to give a second crop which was combined with the first to give after drying the title compound:

$^1$H NMR (CD$_3$OD) d 4.07 (s, 2 H), 6.88 (d, J=8.6 Hz, 1 H), 7.25 (dd, J=2.6 and 8.6 Hz, 1H), 7.31 (d, J=2.6 Hz, 1 H).

Step C: N-t-Butoxycarbonyl-2-Hydroxy-5-Chlorobenzylamine

A mixture of 2-hydroxy-5-chlorobenzylamine (1.22 g, 4.77 mmol assuming the bisulfate salt), (BOC)$_2$O (1.56 g, 7.16 mmol) and N-methylmorpholine (1.05 ml, 9.54 mmol) in DMF (10 ml) was stirred for 5 h at r.t. The reaction was partitioned between water and ethyl acetate and the organic layer was washed with 5% KHSO$_4$ solution (2 times), sodium hydrogen carbonate solution and brine, dried (Na$_2$SO$_4$) and evaporated in vacuo to a solid. The crude product was recrystallized from ethyl acetate/hexanes (1:5, 12 ml) to give the title compound:

$^1$H NMR (CDCl$_3$) d 1.44 (s, 9 H, t-Bu), 4.17 (d, J=6.8 Hz, 2H, CH$_2$), 5.22 (br t, 1H, NH), 6.87 (d, J=8.6 Hz, 1H, H-3), 7.03 (d, J=2.6 Hz, 1H, H-6), 7.15 (dd, J=2.6 and 8.6 Hz, 1H, H-4).

Step D: Ethyl-(2-t-Butoxycarbonylaminomethyl-4-Chlorophenoxy)-Acetate

A mixture of N-t-butoxycarbonyl-2-hydroxy-5-chlorobenzylamine (730 mg, 2.83 mmol), Cs$_2$CO$_3$ (923 mg, 2.83 mmol) and ethylbromoacetate (0.314 ml, 2.83 mmol) in DMF (5 ml) was stirred for 2 h. The crude reaction mixture was partitioned between ethyl acetate and water and the organic layer was washed with brine, dried (Na$_2$SO$_4$) and evaporated in vacuo to an oil which was used for the next step.

Step E: 2-t-Butoxycarbonylaminomethyl-4-Chlorophenoxyacetic Acid

The product from Step D was suspended in 1:1:1 methanol/THF/water (9 ml) and lithium hydroxide hydrate (126 mg, 3.0 mmol) was added. After 16 h the volatiles were removed in vacuo and the solution was diluted with water and was washed with ethyl acetate, adding sufficient brine to disperse the emulsion. The aqueous layer was acidified with 5% KHSO$_4$ solution and was extracted with methylene chloride which was then dried (Na$_2$SO$_4$) and evaporated in vacuo to give the title compound as a solid:

$^1$H NMR (CDCl$_3$) d 1.44 (s, 9H, t-Bu), 4.35 (br s, 2H, NCH$_2$), 4.62 (s, 2H, OCH$_2$), 5.04 (br s, 1H, NH), 6.74 (d, J=7.9 Hz, 1H, H-3), 7.20 (d, J=2.6 Hz, 1H, H-6), 7.24 (d obscured, 1H, H-4).

Step F: Ethyl-(2-t-Butoxycarbonylaminomethyl-4-Chlorophenoxy)-Acetamide

EDC Hydrochloride (249 mg, 1.3 mmol) was added to a stirred mixture of 2-t-butoxycarbonylaminomethyl-4-chlorophenoxyacetic acid (316 mg, 1.0 mmol), HOBT (176 mg, 1.3 mmol), ethylamine hydrochloride (106 mg, 1.3 mmol) and N-methylmorpholine (0.396 ml, 3.6 mmol) in DMF (4 ml) and the mixture was stirred for 16 h. The reaction was partitioned between ethylacetate and 5% KHSO$_4$ solution and the organic layer was washed with 5% KHSO$_4$ solution, water, NaHCO$_3$ solution and brine, dried (Na$_2$SO$_4$) and evaporated in vacuo to a solid (333 mg) which was used for the next step.

Step G: Ethyl-(2-Aminomethyl-4-Chlorophenoxy)-Acetamide

Ethyl-(2-t-butoxycarbonylaminomethyl-4-chlorophenoxy)-acetamide from Step F was dissolved in 2:1 methylene chloride/TFA (3 ml) and after 15 min the solvent was evaporated in vacuo. The residue was dissolved in water and the solution was washed with methylene chloride (twice). The aqueous layer was then basified with saturated sodium carbonate solution and NaCl was added to saturation. The mixture was extracted with ethyl acetate, and the organic layer was dried (Na$_2$SO$_4$) and evaporated in vacuo to give the title compound as a crystalline solid:

$^1$H NMR (300 MHz, CDCl$_3$) d 1.12 (t, J=7.3 Hz, 3H, Me), 1.54 (s, 9H, t-Bu), 3.31 (quintet, J=7.3 Hz, 2H, CH$_2$Me), 3.90 (s, 2H, NCH$_2$), 4.58 (s, 2H, OCH$_2$), 6.80 (d, J=8.3 Hz, 1H, H-3), 7.19–7.23 (m, 2H, H-4, H-6), 8.01 (br s, 1H, CONH).

METHOD 2 (as exemplified by Example III)

The product of METHOD 1, Step A is alkylated with an acetate equivalent such as ethyl bromoacetate in Step A which is then reacted with the thiol in Step B. The ester is then hydrolysed in Step C with lithium hydroxide and the resulting carboxylic acid is coupled with the appropriate amine, in this case 5-aminomethyl-2-t-butoxycarbonylamino-6-methylpyridine (a method for the preparation of this amine is shown below) in Step D. The nitro group is reduced in Step E with hydrogen in the presence of a catalyst such as palladium on carbon and the BOC group removed by a strong acid such as HCl in Step F to give the final product.

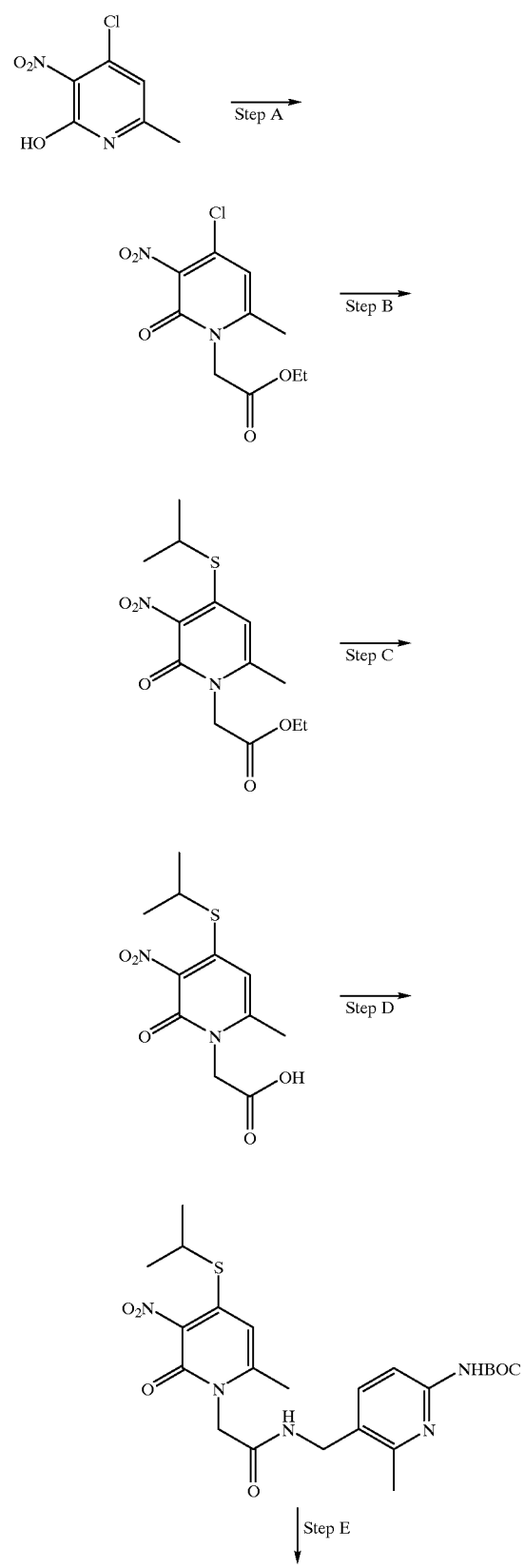

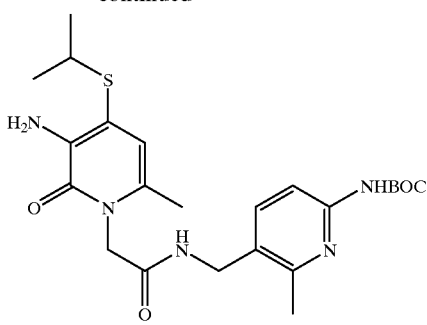

Step F

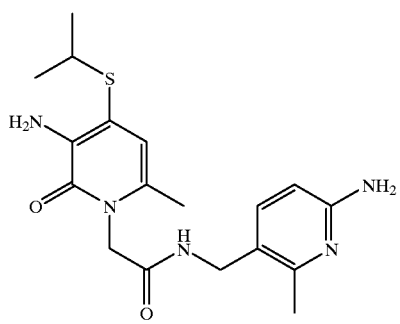

Modifications of METHODS 1 and 2 will allow different W, $R^2$, $R^3$ and A groups contemplated by the scope of the broad claim below to be present by the use of an appropriate reagent or appropriately substituted starting material in the indicated synthetic step. For example the starting pyridine in Step A can have as its side chain at the 6-position, ethyl, isopropyl, cyclopropyl, trifluoromethyl, and the like, to achieve the different operable values of $R^3$. Similarly the thiol in Step B can have as its $R^2$ group, benzyl, cyclopropylmethyl, and the like, to achieve the different operable values of $R^2$. An appropriate choice of the amine in the coupling step will allow the different operable values of A to be achieved. Different W groups may be introduced by such methods as alkylation, acylation or sulfonylation of the products of METHOD 1, Step F and METHOD 2, Step E. Obvious variations and modifications of the method to produce similar and obvious variants thereof, will be apparent to one skilled in the art.

Method for Making 5-aminomethyl-2-t-butoxycarbonylamino-6-methylpyridine

Preparation of 2-Amino-5-cyano-6-methylpyridine

A mixture of 2-amino-5-bromo-6-methylpyridine (20.0 g, 0.107 mol) (Maybridge) and copper (I) cyanide 11.0 g, 0.123 mol) in DMF (25 ml) was heated to reflux for 4 h. The DMF was evaporated in vacuo and the residue was partitioned between ethyl acetate and 10% sodium cyanide solution. The organic layer was washed with 10% sodium cyanide solution and brine, dried ($Na_2SO_4$) and evaporated in vacuo to a brown solid. This was dissolved in a minimum amount of ethyl acetate and the product was precipitated by adding hexanes. The mixture was filtered to give the title compound as a brown powder:

$^1$H NMR (CDCl$_3$) d 2.56 (s, 3 H), 4.97 (br s, 2 H), 6.33 (d, J=8.6 Hz, 1 H), 7.54 (d, J=8.6 Hz, 1 H).

Preparation of 2-t-Butoxycarbonylamino-5-cyano-6-methylpyridine

A mixture of 2-amino-5-cyano-6-methylpyridine (10.0 g, 75.1 mmol), (BOC)$_2$O (16.39 g, 75.1 mmol), triethylamine (11.5 ml, 82.6 mmol) and DMAP (0.92 g, 7.5 mmol) in methylene chloride (200 ml) was stirred for 3 h. More triethylamine (4.22 ml) and (BOC$_2$)O (1.64 g) were added and after 16 h the reaction was diluted with ethyl acetate and was washed with 1 M AcOH (3 times), dried (Na$_2$SO$_4$) and evaporated in vacuo to give dark brown solid. The crude product was purified by flash column chromatography (10% ethylacetate/hexanes) to give the title compound as a white solid:

$^1$H NMR (CDCl$_3$) d 1.52 (s, 9 H), 2.62 (s, 3 H), 7.46 (br s, 1 H), 7.80 (d, J=8.8 Hz, 1 H), 7.88 (d, J=8.8 Hz, 1 H).

Preparation of 5-aminomethyl-2-t-butoxycarbonylamino-6-methylpyridine

A mixture of 2-t-butoxycarbonylamino-5-cyano-6-methylpyridine (14.68 g, 62.9 mmol) and 10% Pd/C (1.5 g) in glacial acetic acid (150 ml) was shaken on a Parr apparatus at 60 psi for 88 h. The reaction was filtered through celite and was evaporated in vacuo. The residue was dissolved in water and the solution was washed with methylene chloride (2 times), then was basified with sodium carbonate and extracted with ethyl acetate (2 times). The combined ethyl acetate layers were dried (Na$_2$SO$_4$) and evaporated in vacuo to a solid. The crude product was recrystallized (ethyl acetate/hexanes) to give the title compound:

$^1$H NMR (CDCl$_3$) d 1.50 (s, 9 H), 2.43 (s, 3 H), 3.81 (s, 2 H), 7.23 (br s, 1 H), 7.57 (d, J=8.3 Hz, 1 H), 7.70 (d, J=8.3 Hz, 1 H).

Modifications of this method will allow different $R^{12}$ and $R^{13}$ groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 3 (as exemplified by Example X)

The product of METHOD 2, Step B, in this case where $R^2$ is benzyl, is reduced in Step A with a reducing agent such as iron in acetic acid to give the amine. The ester is then hydrolysed and coupled with the appropriate amine, in this case 2-amino-5-aminomethyl- 6-methylpyridine (a method for the preparation of this amine is shown below) in Step B to give the final product.

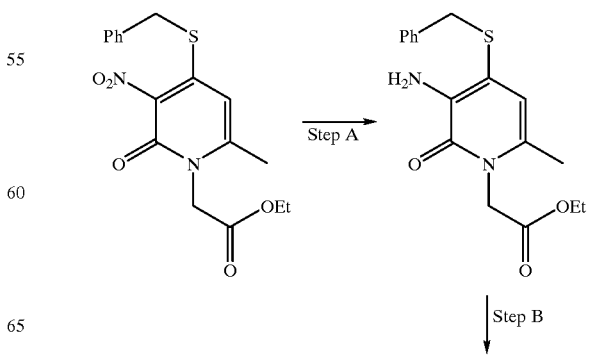

Step B

-continued

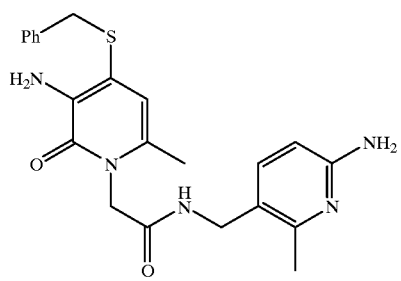

Modifications of this Method will allow different W, $R^2$, $R^3$ and A groups contemplated by the scope of the broad claim below to be present by the use of an appropriate reagent or appropriately substituted starting material in the indicated synthetic step. For example the starting pyridinone in Step A can have as its side chain at the 6-position, ethyl, isopropyl, cyclopropyl, trifluoromethyl, and the like, to achieve the different operable values of $R^3$. Similarly it can have as its $R^2$ group, phenyl, cyclopropylmethyl, and the like, to achieve the different operable values of $R^2$. An appropriate choice of the amine in Step C will allow the different operable values of A to be achieved. Different W groups may be introduced by such methods as alkylation, acylation or sulfonylation of the product of Step A. Obvious variations and modifications of the method to produce similar and obvious variants thereof, will be apparent to one skilled in the art.

Preparation of 2-Amino-5-methylamino-6-methylpyridine dihydrochloride

A mixture of 2-amino-5-cyano-6-methylpyridine (4.0 g, 30.0 mmol) and 10% Pd/C (3.08 g) in ethanol (80 mL), methanol (30 mL), concentrated HCl (6 mL) and water (10 mL) was shaken on a Parr apparatus at 60 psi for 25 h. The reaction was filtered through celite, rinsing with 1:1 ethanol/methanol and was evaporated in vacuo to a solid, which was triturated with 5:1 ethyl acetate/ethanol to give the title compound (5.95 g, 94%):

$^1$H NMR (CD$_3$OD): d 2.58 (s, 3 H), 4.12 (s, 2 H), 6.92 (d, J=9.2 Hz, 1 H), 7.93 (d, J=9.2 Hz, 1 H).

Modifications of this method will allow different $R^{12}$ and $R^{13}$ groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 4 (as exemplified by Example IV)

The product of METHOD 2, Step A is reacted with a sulfinate salt in this case were $R^2$ is cyclopropylmethyl in a solvent such as ethanol or DMF in Step A to give the sulfone. The nitro group may be reduced in Step B with hydrogen in the presence of a catalyst such as palladium on carbon, the ester hydrolysed in Step C and the resulting carboxylic acid coupled to with the appropriate amine, in this case 2-amino-5-aminomethyl-6-methylpyridine, in Step D to give the final product.

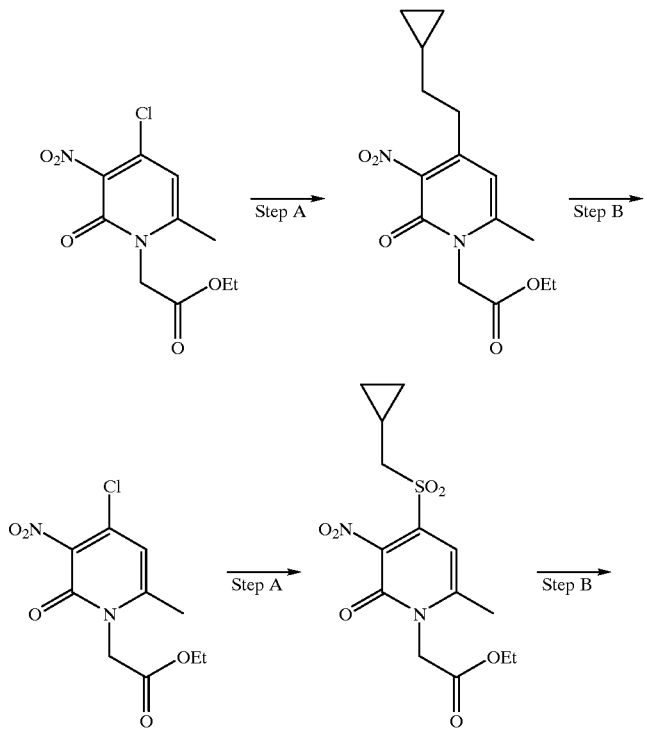

-continued

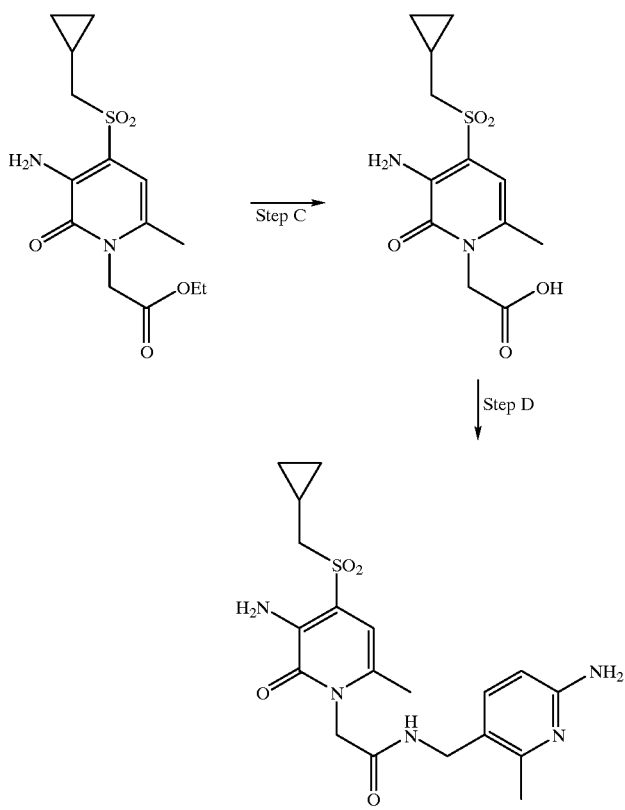

Sulfinate salts used in the preparation of compound of the invention may be generated from the sulfinic acids. They may also be generated by a number of other methods, including the reductive cleavage of 2-sulfonylbenzothiazoles, the reaction of organometallics with sulfur dioxide, the reduction of sulfonyl chlorides, the oxidation of thiols and the cleavage of phthalimidomethyl sulfones.

Modifications of this method will allow different W, $R^2$, $R^3$ and A groups contemplated by the scope of the broad claim below to be present by the use of an appropriate reagent or appropriately substituted starting material in the indicated synthetic step. For example the starting pyridinone in Step A can have as its side chain at the 6-position, ethyl, isopropyl, cyclopropyl, trifluoromethyl, and the like, to achieve the different operable values of $R^3$. Similarly the sulfinate in Step A can have as its $R^2$ group, benzyl, cyclopentyl, and the like, to achieve the different operable values of $R^2$. An appropriate choice of the amine in Step D will allow the different operable values of A to be achieved. Different W groups may be introduced by such methods as alkylation, acylation or sulfonylation of the product of Step B. Obvious variations and modifications of the method to produce similar and obvious variants thereof, will be apparent to one skilled in the art.

METHOD 5 (as exemplified by Example VIIb)

The product of METHOD 2, Step B, in this case where $R^2$ is benzyl, may be oxidized with a suitable oxidizing agent such as OXONE® or a peracid such as mCPBA to give the sulfone which may be further manipulated, for example by the procedures of METHOD 4, Steps B–D, to give the products of the invention.

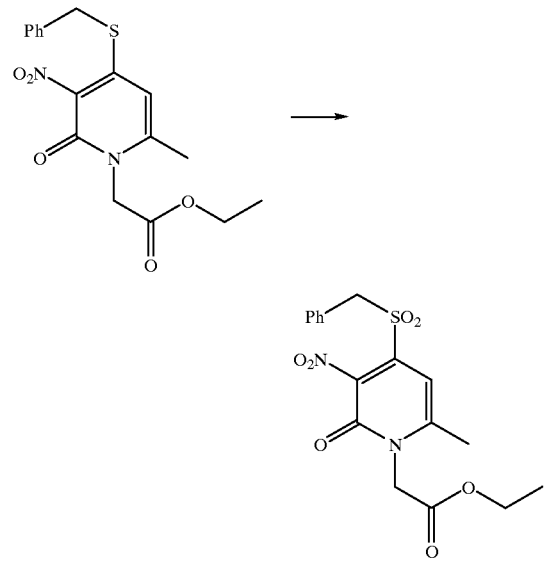

The compounds of the present invention, where X is $CR^{15}R^{16}$, may be prepared using METHODS 6 and 7:

METHOD 6 (as exemplified by Example XI)

The starting 2-hydroxy-3-nitropyridine is alkylated with an acetate equivalent such as t-butyl bromoacetate in Step A to give the pyridinone. This is reacted with an organomagnesium reagent, in this case cyclohexylmethyl magnesium bromide, in Step B. The resulting lactam is oxidised in Step C with an oxidising agent such as DDQ or nickel peroxide to regenerate the pyridinone. The t-butyl group is removed using a strong acid such as HCl in Step D and the resulting carboxylic acid coupled with the appropriate amine, in this case 2-BOC-amino-5-aminomethyl-6-methylpyridine in Step E. The nitro group is reduced in Step F by hydrogenation using a catalyst such as palladium on carbon and the the BOC group is removed in Step G with a strong acid such as TFA to give the final product.

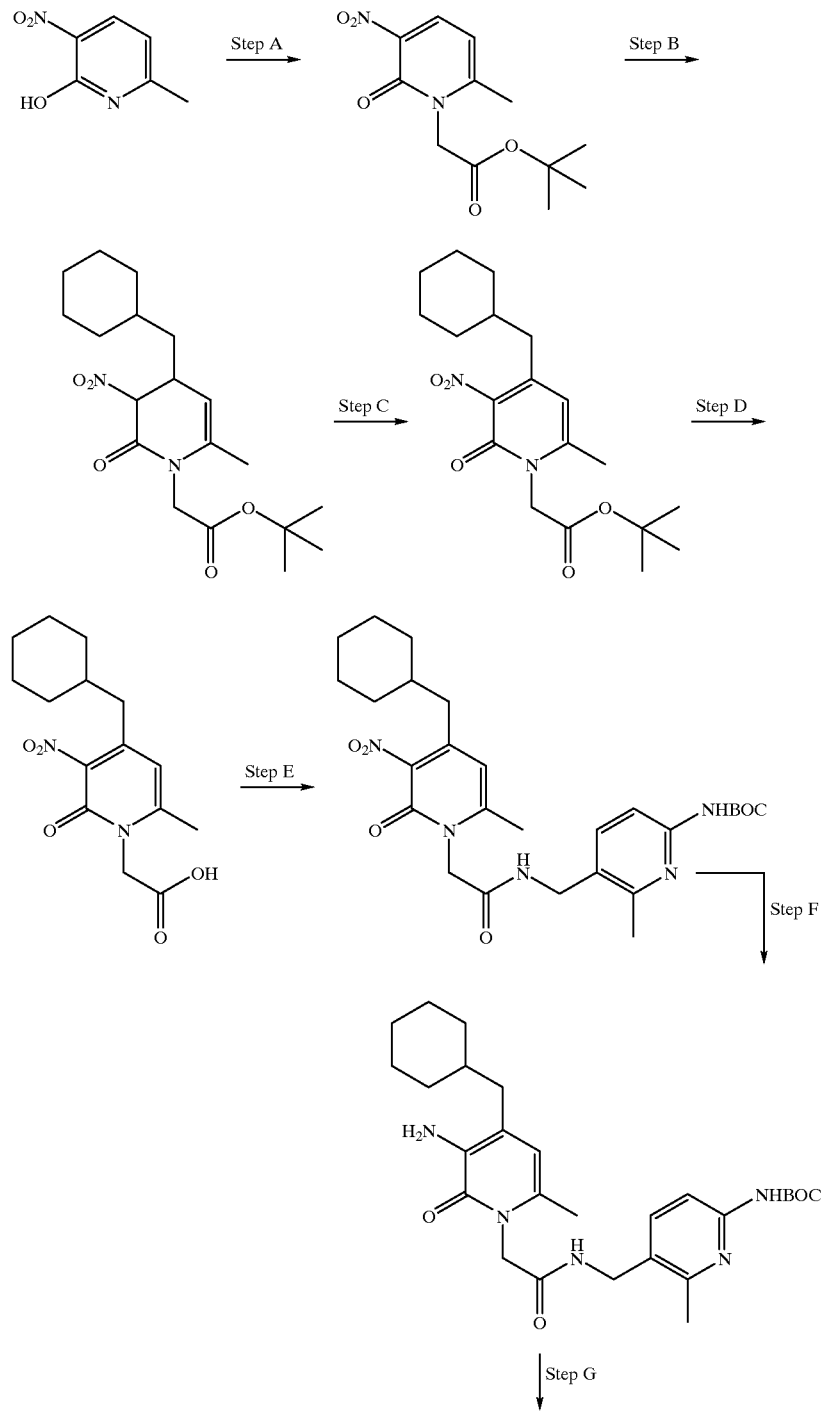

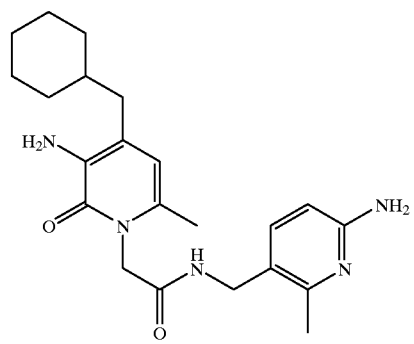

METHOD 7 (as exemplified by Example I)

The starting acid is esterified in Step A and is alkylated with t-butyl bromoacetate in Step B. The resulting pyridinone is reacted with an organomagnesium reagent, in this case benzyl magnesium chloride, in Step C and the lactam is oxidised in Step D with an oxidising agent such as DDQ or nickel peroxide to regenerate the pyridinone. The t-butyl group is removed using a strong acid such as TFA in Step E and the resulting carboxylic acid coupled with the appropriate amine, in this case 2-BOC-amino-5-aminomethyl-6-methylpyridine in Step F. The ethyl ester is hydrolysed with lithium hydroxide in Step G and the acid was rearranged to the isocyanate via the acyl azide using DPPA and a base such as triethylamine followed by heating in Step H. The intermediate isocyanate is then reacted with benzyl alcohol in the presence of a base to give the CBZ derivative. The CBZ group was removed by hydrogenolysis in Step I using a catalyst such as palladium and the amine is then sulfonylated in Step J, in this case with methane sulfonyl chloride, in the presence of a base such as pyridine. The BOC group is removed in Step K with a strong acid such as TFA to give the final product.

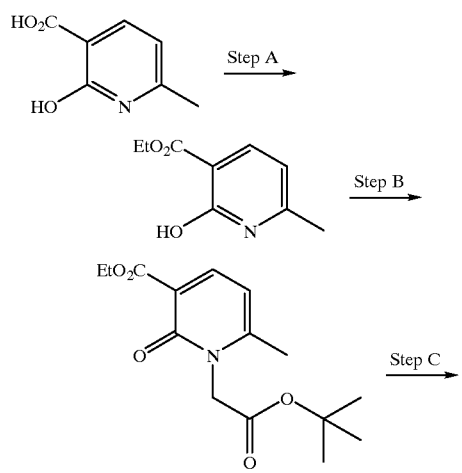

-continued

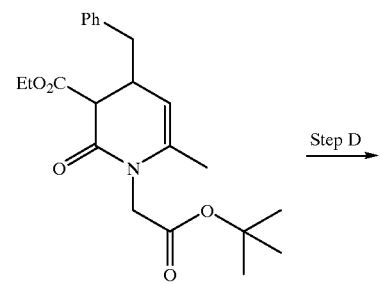

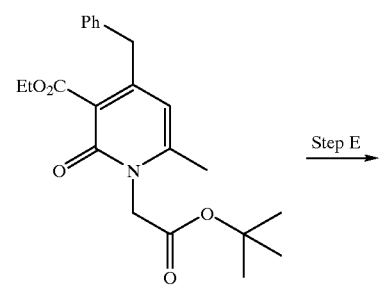

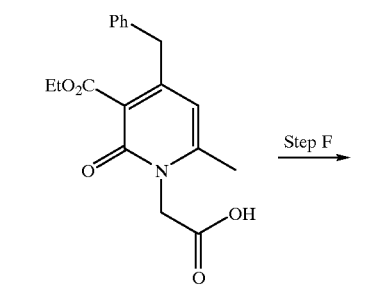

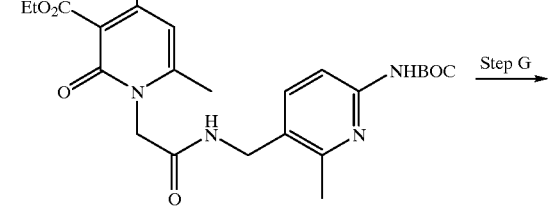

-continued

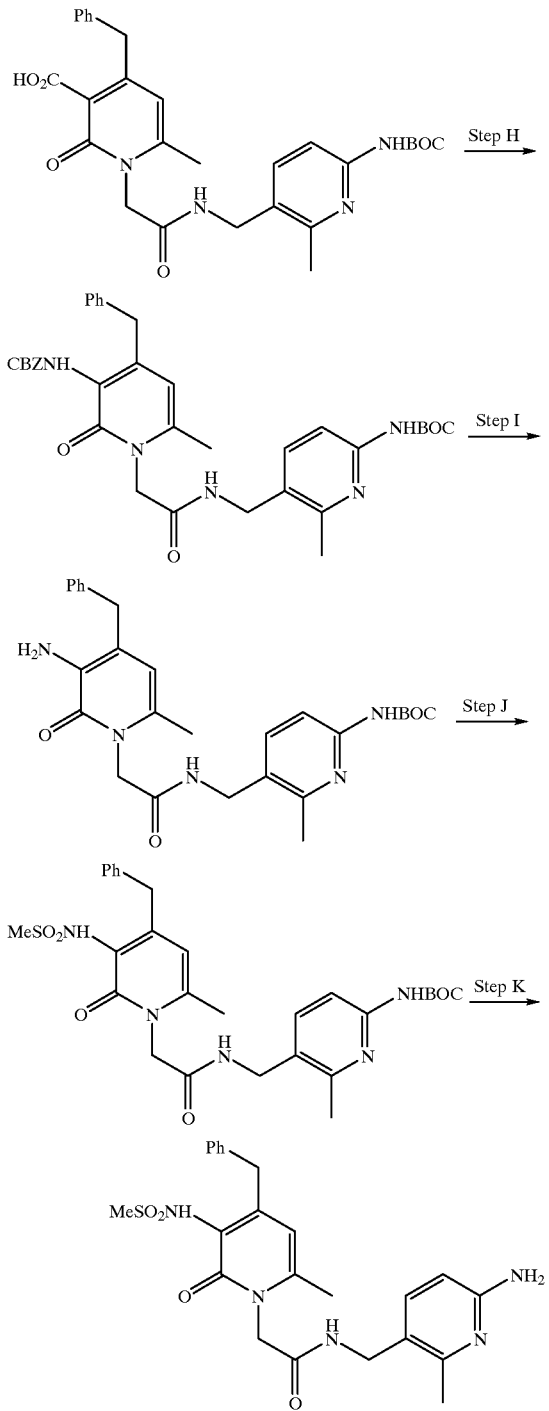

Modifications of METHODS 6 and 7 will allow different W, $R^2$, $R^3$ and A groups contemplated by the scope of the broad claim below to be present by the use of an appropriate reagent or appropriately substituted starting material in the indicated synthetic step. For example the starting pyridine can have as its side chain at the 6-position, ethyl, isopropyl, cyclopropyl, trifluoromethyl, and the like, to achieve the different operable values of $R^3$. Different operable values of $R^2$ may be acheived by the appropriate choice of the organometallic reagent. An appropriate choice of the amine in the coupling step will allow the different operable values of A to be achieved. Different W groups may be introduced by such methods as alkylation, acylation or sulfonylation of the products from METHOD 6, Step F, and METHOD 7, Step I. Obvious variations and modifications of the method to produce similar and obvious variants thereof, will be apparent to one skilled in the art.

Amide couplings to form the compounds of this invention can be performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

The following examples are illustrative of the invention as contemplated by the inventors and should not be construed as being limits on the scope or spirit of the instant invention.

EXAMPLE I

Preparation of 3-Methanesulfonylamino-4-benzyl-6-methyl-1-(2-amino-6-methyl-5-methylenecarboxamidomethylpyridinyl)-2-pyridinone

I-11

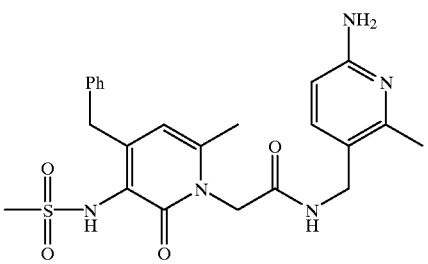

Step A: Ethyl 6-methylpyridin[1H]-2-one-3-carboxylate (I-1)

To a stirred slurry of 7.66 g (50 mmol) of 2-hydroxy-6-methylpyridine-3-carboxylic acid, 3.52 mL (60 mmol) of anhydrous ethanol, and 611 mg (5 mmol) of 4-(N,N-dimethylamino)pyridine (DMAP) in 100 mL of $CH_2Cl_2$ was added 10.32 g (50 mmol) of dicyclohexylcarbodiimide (DCC) and the mixture stirred overnight at ambient temperature. The mixture was filtered and the precipitate was washed with minimal $CH_2Cl_2$. The filtrate was concentrated and crystallized from 100 mL of ethyl acetate to give I-1 as a colorless solid:

$^1$H NMR (CDCl$_3$) ∂ 8.15 (d, 1H, 7.5 Hz), 6.3 (br s, 1H), 4.37 (q, 2H, 7.1 Hz), 2.46 (s, 3H), 1.38 (t, 3H, 7.1 Hz).

Step B: Ethyl 6-methyl-1-(t-butyl acetate)pyridin[1H]-2-one-3-carboxylate (I-2)

To a 0° C. stirred suspension of 3.5 g (19.3 mmol) of ethyl 6-methylpyridin-2-one-3-carboxylate in 50 mL anhydrous THF under Ar was added 0.8 g (20 mmol) of NaH (60% in oil) in portions over a 2 min period. After the mixture became homogeneous over 10 min, 3.55 mL (22 mmol) of t-butyl bromoacetate was added dropwise. The cold bath was removed and the reaction mixture stirred under Ar overnight. Concentration of the reaction mixture at reduced pressure gave a residue that was partitioned between CHCl$_3$ and 1M citric acid. The aq. layer was extracted with CHCl$_3$, and the combined organic layers washed with 10% Na$_2$CO$_3$, dried over Na$_2$SO$_4$ and the solvents removed to give an oil that was chromatographed on 75 g of SiO2 using 98.5:1.5 to 95:5 CHCl$_3$—CH$_3$OH which gave 1–2 as a colorless solid:

$^1$H NMR (CDCl$_3$) ∂ 8.1 (d, 1, 7.3 Hz), 6.13 (d, 1H, 7.3 Hz), 4.78 (s, 2H), 4.35 (q, 2H, 7.1 Hz), 2.34 (s, 3H), 1.48 (s, 9H), 1.37 (t, 3H, 7.1 Hz).

Step C: Ethyl 4-benzyl-3,4-dihydro-6-methyl-1-(t-butyl acetate)pyridin[1H]-2-one-3-carboxylate (I-3)

To a stirred −78° solution of 1.0 g (3.39 mmol) of ethyl 6-methyl-1-(t-butyl acetate)pyridin-2-one-3-carboxylate in 20 mL of anhydrous THF was added a 2M THF solution of benzylmagnesium chloride dropwise. After stirring for 15 min at −78°, the reaction was stored in the freezer (approx. −15° C.) overnight. After quenching with 200 μL (3.5 mmol) of acetic acid, the reaction was concentrated at reduced pressure, diluted with cold 5% HCl and extracted with EtOAc. The organic layer was washed with sat. NaHCO$_3$, brine, dried over Na$_2$SO$_4$ and concentrated at reduced pressure to give an oil that was chromatographed on 50 g SiO$_2$ using 11:29 EtOAc-hexane. Concentration of the fractions at reduced pressure provided I-3 as a colorless oil:

$^1$H NMR (CDCl$_3$) ∂ 7.35–7.15 (m, 5H), 4.94 (d, 1H, 4.4 Hz), 4.54 (d, 1H, 17.5 Hz), 4.3–4.1 (m, 2H), 4.08 (d, 1H, 17.6 Hz), 3.35 (d, 1H, 7.3 Hz), 3.15–3.05 (m, 1H), 2.8–2.65 (m, 2H), 1.83 (t, 3H, 1.3 Hz), 1.47 (s, 9H), 1.25 (t, 3H, 7.1 Hz).

Step D: Ethyl 4-benzyl-6-methyl-1-(t-butyl acetate)pyridin[1H]-2-one-3-carboxylate (I-4)

To a stirred solution of 690 mg (1.78 mmol) of ethyl 4-benzyl-3,4-dihydro-6-methyl-1-(t-butyl acetate)pyridin[1H]-2-one-3-carboxylate in 7 mL of dioxane was added 445 mg (1.95 mmol) of 2,5-dichloro- 3,6-dicyano-1,4-benzoquinone (DDQ). After heating at 70° C. for 24 h under Ar, the cooled reaction mixture was diluted with 21 mL of benzene and the precipitate removed by filtration. Concentration at reduced pressure, followed by chromatography of the residue on 15 g SiO$_2$ using 1:2 to 2:3 EtOAc-hexane provided I-4 as a pale yellow solid:

$^1$H NMR (CDCl$_3$) ∂ 7.35–7.2 (m, 5H), 5.81 (s, 1H), 4.69 (s, 2H), 4.34 (q, 2H, 7.1 Hz), 3.82 (s, 2H), 2.19 (s, 3H), 1.46 (s, 9H), 1.31 (t, 3H, 7.1 Hz).

Step E: Ethyl 4-benzyl-6-methyl-1-carboxymethylpyridin[1H]-2-one-3-carboxylate (I-5)

To a stirred solution of 456 mg (1.18 mmol) of ethyl 4-benzyl-6-methyl-1-(t-butyl acetate)pyridin[1H]-2-one-3-carboxylate in 30 mL of CH$_2$Cl$_2$ was added 15 mL of trifluoroacetic acid (TFA). After stirring for 4 h under Ar, the reaction mixture was concentrated, dissolved in 30 mL of DMF and re-concentrated to give I-5, a sticky yellow solid which was used directly in the following reaction.

Step F: 4-Benzyl-3-(ethoxycarbonyl)-6-methyl-1-(2-t-butyloxycarbonylamino-6-methyl-5-methylenecarboxamidomethylpyridinyl) pyridin[1H]-2-one (I-6)

To a stirred solution of 200 mg (0.61 mmol) of ethyl 4-benzyl-6-methyl-1-carboxymethylpyridin[1H]-2-one-3-carboxylate and 144 mg (0.61 mmol) of 2-t-butyloxycarbonylamino-5-aminomethyl-6-methylpyridine in 10 mL of CH$_2$Cl$_2$ was added 126 mg (0.61 mmol) of dicyclohexylcarbodiimide (DCC) under Ar. After stirring for 3 h, the precipitate that had formed was removed by filtration, washed with minimal CH$_2$Cl$_2$, and the filtrate was diluted and washed with 1M citric acid, 5% NaHCO$_3$, dried over Na$_2$SO$_4$ and concentrated at reduced pressure to give I-6 as a pale yellow solid:

$^1$H NMR (CDCl$_3$) ∂ 7.64 (d, 1H, 8.4 Hz), 7.41 (d, 1H, 8.4 Hz), 7.35–7.2 (m, 5H), 7.09 (s, 1H), 5.90 (s, 1H), 4.65 (br s, 2H), 4.4–4.3 (m, 4H), 3.83 (s, 2H), 2.41 (s, 3H), 2.36 (s, 3H), 1.51 (s, 9H), 1.32 (t, 3H, 7.1 Hz).

Step G: 4-Benzyl-3-carboxy-6-methyl-1-(2-t-butyloxycarbonylamino-6-methyl-5-methylenecarboxamidomethylpyridinyl) pyridin[1H]-2-one (I-7)

A 348 mg (0.63 mmol) sample of 4-benzyl-3-(ethoxycarbonyl)-6-methyl-1-(2-t-butyloxycarbonylamino-6-methyl-5-methylenecarboxamidomethylpyridinyl) pyridin[1H]-2-one was dissolved in 10 mL of 1,2-dimethoxyethane and treated with 2.5 mL of 1M LiOH under Ar for 16 h at 40° C. The reaction mixture was concentrated at reduced pressure and partitioned between EtOAc and 1M citric acid. The organic layer was washed with water, brine, dried over Na$_2$SO$_4$ and concentrated at reduced pressure to give I-7 as a yellow solid which was used directly in the following reaction.

Step H: 4-Benzyl-3-(benzyloxycarbonylamino)-6-methyl-1-(2-t-butyloxycarbonylamino-6-methyl-5-methylenecarboxamidomethylpyridinyl) pyridin[1H]-2-one (I-8)

A solution of 281 mg (0.54 mmol) of 4-benzyl-3-carboxy-6-methyl-1-(2-t-butyloxycarbonylamino-6-methyl-5-methylenecarboxamidomethylpyridinyl) pyridin[1H]-2-one, 117 μL (0.54 mmol) of diphenylphosphoryl azide, and 75 μL (0.54 mmol) of triethylamine (TEA) were heated to 50–60° C. in 3 mL of dioxane under Ar for 20 h. Benzyl alcohol (61 μL, 0.59 mmol) and a second portion of triethylamine were added and heating continued for 20 h. The reaction mixture was concentrated at reduced pressure and partitioned between CHCl$_3$ and 1M citric acid. The aqueous layer was extracted with CHCl$_3$ and the combined organic layers were washed with 10% Na$_2$CO$_3$, dried over Na$_2$SO$_4$ and the solvents removed to give an oil that was chromatographed on 20 g SiO$_2$ using 95:5 CHCl$_3$/CH$_3$OH to give I-8 as a green tinted oil:

$^1$H NMR (CDCl$_3$) ∂ 7.64 (d, 1H, 8.3 Hz), 7.42–7.2 (m, 10H), 6.68 (br s, 1H), 5.85 (s, 1H), 5.16 (s, 2H), 4.64 (s, 2H), 4.29 (d, 2H, 5.6 Hz), 3.88 (s, 2H), 2.34 (s, 3H), 2.33 (s, 3H), 1.50 (s, 9H).

Step I: 4-Benzyl-3-amino-6-methyl-1-(2-t-butyloxycarbonylamino-6-methyl-5-methylenecarboxamidomethylpyridinyl) pyridin[1H]-2-one (I-9)

A stirred solution of 185 mg (0.3 mmol) of 4-benzyl-3-(benzyloxycarbonylamino)-6-methyl-1-(2-t-butyloxycarbonylamino-6-methyl-5-methylenecarboxamidomethylpyridinyl) pyridin[1H]-2-one in 11 mL of ethanol was hydrogenated with 41 mg of 20% Pd(OH)$_2$ on carbon using a balloon overnight. The catalyst was removed by filtration, washed with ethanol, and the filtrate concentrated at reduced pressure to give I-9 as an oily residue which was carried forward to the next step.

Step J: 4-Benzyl-3-(methanesulfonylamino)-6-methyl-1-(2-t-butyloxycarbonylamino-6-methyl-5-methylenecarboxamidomethylpyridinyl) pyridin[1H]-2-one (I-10)

The product from Step I was dissolved in 3 mL of pyridine, cooled in an ice bath and treated with 28 μL (0.36 mmol) of methanesulfonyl chloride dropwise. The cold bath was allowed to expire over a 2.5 h period, the reaction concentrated at reduced pressure, partitioned between CHCl$_3$ and 1M citric acid. The organic layer was washed with 5% NaHCO$_3$, dried over Na$_2$SO$_4$, treated with activated carbon and concentrated to give a yellow oil that was chromatographed on 14 g of SiO$_2$ using 99:1 to 97:3 CHCl$_3$—CH$_3$OH to afford I-10 as a colorless solid:

$^1$H NMR (CDCl$_3$) ∂ 7.69 (d, 1H, 8.1 Hz), 7.58 (br s, 1H), 7.45 (d, 1H, 8.4 Hz), 7.35–7.23 (m, 3H), 7.17 (d, 2H, 6.8 Hz), 6.94 (br t, 1H), 6.56 (s, 1H), 5.91 (s, 1H), 4.64 (s, 2H), 4.37 (d, 2H, 5.5 Hz), 4.13 (s, 2H), 2.82 (s, 3H), 2.39 (s, 3H), 2.35 (s, 3H), 1.51 (s, 9H).

Step K: 4-Benzyl-3-methanesulfonylamino-6-methyl-1-(2-amino-6-methyl-5-methylenecarboxamidomethylpyridinyl) pyridin[1H]-2-one (I-11)

To a stirred solution of 60 mg (0.1 mmol) of 4-benzyl-3-(methanesulfonylamino)-6-methyl-1-(2-t-butyloxycarbonylamino-6-methyl-5-methylenecarboxamidomethylpyridinyl) pyridin[1H]-2-one in 8 mL of CH2Cl2 was added 4 mL of TFA under Ar. After stirring for 45 min, the reaction was concentrated at reduced pressure and retreated with TFA as above for an additional 30 min. The reaction was concentrated at reduced pressure and purified by gradient elution preparative HPLC using a C-18 stationary phase and 0.1% aqueous TFA/CH$_3$CN as the mobile phase. The fractions were assayed by analytical HPLC, combined and concentrated at reduced pressure to give a residue that was triturated with 1:4 EtOAc-hexane to provide I-11 as a colorless solid:

$^1$H NMR (D$_6$-DMSO) ∂ 13.55 (br s, 1H), 8.75 (br s, 2H), 7.74 (d, 1H, 7 Hz), 7.55 (br s, 2H), 7.4–7.15 (m, 5H), 6.76 (d, 1H, 7 Hz), 5.90 (s, 1H), 4.63 (s, 2H), 4.15 (br d, 2H), 3.95 (s, 2H), 2.98 (s, 3H), 2.40 (s, 3H), 2.18 (s, 3H).

EXAMPLE II

3-Amino-4-Phenylthio-6-Methyl-1-[Cyclopropyl-(2-Methylenecarboxamidomethyl-4-Chlorophenoxy)-Acetamido]-2-Pyridinone

II-6

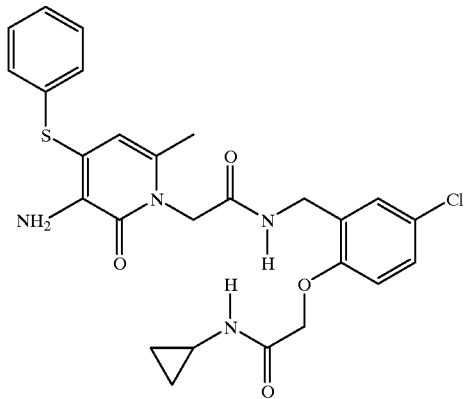

Step A: 4-Chloro-2-hydroxy-6-methyl-3-nitropyridine (II-1)

POCl3 (7.6 mL, 81.4 mmol) was added to a solution of 2,4-hydroxy-6-methyl-3-nitropyridine (Fluka, 3.15 g, 18.5 mmol) and BnEt3NCl (16.8 g, 74 mmol) in MeCN (65 mL). The resulting solution was stirred at 40° C. for 30 min then was heated at reflux for 1 h. After evaporation of the solvent, water (70 mL) was added and the mixture was stirred at room temperature for 16 h. The precipitate which formed was filtered and washed with hexane to afford II-1 as a yellow solid.

1H NMR (DMSO-d6) d 2.25 (s, 3H), 6.45 (s, 1H).

Step B: 2-Hydroxy-6-Methyl-3-Nitro-4-Thiophenylpyridine (II-2)

To a solution of 4-chloro-2-hydroxy-6-methyl-3-nitropyridine (188 mg, 1.0 mmol) in 2 mL of EtOH and 0.2 mL (1.4 mmol) of Et3N was added 0.11 mL (1.0 mmol) of PhSH. Precipitation occurred immediately and the solution was allowed to stir at room temperature for 16 h. The solid was filtered and washed with EtOH to afford II-2.

Step C: 1-(t-Butyl-Methylenecarboxy)-6-Methyl-3-Nitro-4-Thiophenyl-2-Pyridinone (II-3)

To a 0° C. solution of 2-hydroxy-6-methyl-3-nitro-4-thiophenylpyridine (171 mg, 0.654 mmol) in 2 mL of DMF was added 17 mg (0.72 mmol) of NaH. The solution was stirred at 0° C. for 10 min before the addition of 0.106 mL (0.72 mmol) of tert-butyl bromoacetate. After 3 h, the solvent was removed in vacuo and the residue was redissolved in 25 mL of EtOAc and washed with water (3×5 mL). The organic phase was dried (MgSO4), concentrated and chromatographed (2/3 EtOAc/Hexane) to afford II-3.

1H NMR (CDCl3) d 7.50 (m, 5H), 5.45 (s, 1H), 4.65 (s, 2H), 2.15 (s, 3H), 1.46 (s, 9H).

Step D: 1-Methylenecarboxy-6-Methyl-3-Nitro-4-Thiophenyl-2-Pyridinone (II-4)

To a 0° C. solution of 1-(t-butyl-methylenecarboxy)-6-methyl-3-nitro-4-thiophenyl-2-pyridinone (77 mg, 0.20 mmol) in 4 mL of DCM was added 1 mL of TFA. The solution was stirred at 0° C. for 3 h, before the solvent was removed in vacuo and the residue was azeotroped with benzene, then EtOAc, then ether to afford II-4.

1H NMR (CDCl3) d 7.50 (m, 5H), 5.45 (s, 1H), 4.75 (s, 2H), 2.10 (s, 3H).

Step E: 6-Methyl-3-Nitro-4-Thiophenyl-1-[Cyclopropyl-(2-Methylenecarboxamidomethyl-4-Chlorophenoxy)-Acetamido]-2-Pyridinone (II-5)

To a solution of 1-methylenecarboxy-6-methyl-3-nitro-4-thiophenyl-2-pyridinone (65.2 mg, 0.204 mmol) and N-cyclopropyl(2-aminomethyl-5-chlorophenoxy)acetamide (59 mg, 0.204 mmol) in 2 mL of DMF was added 39.0 mg (0.204 mmol) of EDCI and 28 mg (0.204 mmol) of HOBT followed by 0.177 mL (1.02 mmol) of DIPEA. The homogeneous mixture was stirred at room temperature for 16 h after which time the solvent was removed under reduced pressure. The residue was disolved in EtOAc and washed with sat'd NaHCO3 then water. The organic phase was dried (MgSO4) and concentrated to afford II-5.

1H NMR (CDCl3) d 8.85 (bt, 1H), 8.00 (bs, 1H), 7.60 (m, 5H), 7.20 (m, 2H), 6.90 (d, J=8.8 Hz, 1H), 5.45 (s, 1H), 4.74 (s, 2H), 4.45 (s, 2H), 4.30 (d, J=4 Hz, 2H), 2.68 (m, 1H), 2.15 (s, 3H), 0.60 (m, 2H), 0.40 (m, 2H).

Step F: 3-Amino-6-Methyl-4-Thiophenyl-1-[Cyclopropyl-(2-Methylenecarboxamidomethyl-4-Chlorophenoxy)-Acetamido]-2-Pyridinone (II-6)

To a solution of 6-methyl-3-nitro-4-thiophenyl-1-[cyclopropyl-(2-methylenecarboxamidomethyl-4-chlorophenoxy)-acetamido]-2-pyridinone (55.2 mg, 0.093 mmol) in 5 mL of EtOAc was added 107 mg (0.475 mmol) of SnCl2.H2O. The mixture was stirred at reflux for 16 h, cooled and made basic by the addition of saturated NaHCO3. The mixture was extracted with saturated NaHCO3 then water. The organic phase was dried (MgSO4) and concentrated to afford II-6 as a white solid.

1H NMR (CDCl3) d 7.65 (bs, 1H), 7.60 (m, 7H), 7.10 (bt, 1H), 6.75 (d, J=8.8 Hz, 1H), 6.00 (s, 1H), 4.68 (s, 2H), 4.55 (s, 1H), 4.40 (m, 3H), 3.50 (d, J=3 Hz, 1H), 2.88 (m, 1H), 2.30 (s, 3H), 0.70 (m, 4H).

EXAMPLE III

Preparation of 3-Amino-4-isopropylthio-6-methyl-1-(2-amino-6-methyl-5-methylenecarboxamidomethylpyridinyl)-2-pyridinone

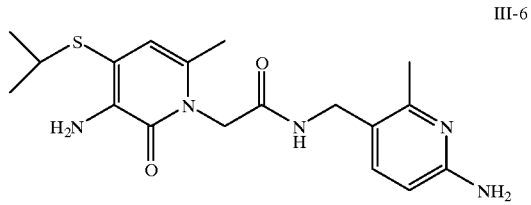

III-6

Step A: 4-Chloro-6-methyl-3-nitro-1-(ethyl-methylenecarboxy)-2-pyridinone (III-1)

Sodium hydride (0.90 g of a 60% dispersion in mineral oil, 22.6 mmol) was added to a stirred solution of 4-chloro-2-hydroxy-6-methyl-3-nitropyridine (4.74 g, 25.1 mmol) in dry DMF (35 mL) at 0° C. under nitrogen. After 20 min ethyl bromoacetate (3.35 mL, 30.2 mmol) was added and the mixture was warmed to room temperature. After 16 h, the solvent was evaporated in vacuo and the residue was partitioned between ethyl acetate and 10% citric acid solution. The organic layer was washed with water and brine, dried (Na2SO4) and evaporated to a heavy oil which was purified by flash column chromatography on silica (60% ethyl acetate/hexanes) to give III-1 as an orange solid.

1H NMR (DMSO-d6) d 1.22 (t, J=7.1 Hz, 3H), 2.41 (s, 3H), 4.18 (q, J=7.1 Hz, 2H), 4.90 (s, 2H), 6.76 (s, 1H).

Step B: 4-Isopropylthio-6-methyl-3-nitro-1-(ethyl-methylenecarboxy)-2-pyridinone (III-2)

To a solution of of 4-chloro-6-methyl-3-nitro-1-(ethyl-methylenecarboxy)-2-pyridinone (500 mg, 1.82 mmol) in 10 mL of EtOH was added 0.22 mL (2.36 mmol) of isopropylthiol followed by 0.37 mL (2.7 mmol) of Et3N. The solution was stirred at 82° C. for 15 h, cooled and evaporated to an oil. The residue was partitioned between EtOAc and water and the organic phase was washed with brine, dried (MgSO4) and concentrated. Column chromatography (3:7 EtOAc/Hexanes) provided III-2 as a white solid.

1H NMR (CDCl3) d 6.13 (s, 1H), 4.79 (s, 2H), 4.25 (q, J=7.4 Hz, 2H), 3.53 (m, 1H), 2.36 (s, 3H), 1.40 (d, J=6.8 Hz, 6H), 1.25 (t, J=7.4 Hz, 3H).

Step C: 4-Isopropylthio-6-methyl-3-nitro-1-methylenecarboxy-2-pyridinone (III-3)

A solution of 4-isopropylthio-6-methyl-3-nitro-1-(ethyl-methylenecarboxy)-2-pyridinone (330 mg, 1.04 mmol) in 5 mL of dioxane and 2 mL of water was treated with 132 mg (3.14 mmol) of LiOH.H2O and the whole was stirred for 15 h. The solvent was removed and the residue was treated with 4 mL of 1N HCl then washed with EtOAc (3×10 mL). The combined organic washings were dried over MgSO4 and evaporated to leave III-3.

1H NMR (CD3OD) d 6.54 (s, 1H), 4.84 (s, 2H), 3.78 (q, J=7.4 Hz, 1H), 2.40 (s, 3H), 1.35 (t, J=7.4 Hz, 3H).

Step D: 4-Isopropylthio-6-methyl-3-nitro-1-(2-t-butyloxycarbonylamino-6-methyl-5-methylenecarboxamidomethylpyridinyl)-2-pyridinone To a solution of 4-isopropylthio-6-methyl-3-nitro-1-methylenecarboxy-2-pyridinone (150 mg, 0.523 mmol) and 2-amino-5-aminomethyl-6-methylpyridine (186 mg, 0.784 mmol) in 2 mL of DMF was added 200 mg (1.04 mmol) of EDCI and 141 mg (1.04 mmol) of HOBT followed by 0.36 mL (2.09 mmol) of DIPEA. The homogeneous mixture was stirred at room temperature for 16 h after which time the solvent was removed under reduced pressure. The residue was disolved in EtOAc and washed with sat'd NaHCO3 then water. The organic phase was dried (MgSO4) and concentrated to afford III-4 as a white solid.

1H NMR (CDCl3) d 7.85 (bt, 1H), 7.44 (d, J=8 Hz, 1H), 7.30 (d, J=8 Hz, 1H), 6.14 (s, 1H), 4.64 (bs, 2H), 4.25 (bs, 2H), 3.68 (q, J=7.4 Hz, 1H), 2.40 (s, 3H), 2.31 (s, 3H), 1.50 (s, 9H), 1.35 (t, J=7.4 Hz, 3H).

Step E: 3-Amino-4-isopropylthio-6-methyl-1-(2-t-butyloxycarbonylamino-6-methyl-5-methylenecarboxamidomethylpyridinyl)-2-pyridinone (III-5)

A solution of 4-isopropylthio-6-methyl-3-nitro-1-(2-t-butyloxycarbonylamino-6-methyl-5-methylenecarboxamidomethylpyridinyl)-2-pyridinone in 10 mL of THF was treated with 62 mg of 10% Pd on carbon and the whole was stirred under an atmosphere of H2 for 16 h. The reaction mixture was filtered through Celite and concentrated to afford III-5 as a tan colored foam which was used without further purification.

1H NMR (CDCl3) d 7.44 (d, J=8 Hz, 1H), 7.55 (s, 1H), 7.50 (bs, 1H), 7.40 (d, J=8 Hz, 1H), 6.11 (s, 1H), 4.70 (bs, 1H), 4.54 (bs, 2H), 4.29 (bs, 2H), 3.39 (m, 1H), 2.30 (s, 3H), 2.25 (s, 3H), 1.50 (s, 9H), 1.35 (d, J=7.4 Hz, 6H).

Step F: 3-Amino-4-isopropylthio-6-methyl-1-(2-amino-6-methyl-5-methylenecarboxamidomethylpyridinyl)-2-pyridinone (III-6)

A solution of 3-Amino-4-isopropylthio-6-methyl-1-(2-t-butyloxycarbonylamino-6-methyl-5-methylenecarboxamidomethylpyridinyl)-2-pyridinone (140 mg, 0.294 mmol) in 10 mL of EtOAc and 5 mL of MeOH was treated with HCl gas for 2 minutes. The flask was capped and the reaction mixture was allowed to stir for 1 h. The solvent was removed and the resulting solid was triturated with ether/EtOAc. The tacky tan solid was filtered to afford III-6 as its bis-HCl salt.

1H NMR (CD3OD) d 8.85 (bt, 1H), 7.85 (d, J=9.5 Hz, 1H), 6.95 (s, 1H), 6.83 (d, J=9.5 Hz, 1H), 6.54 (s, 1H), 4.80 (s, 2H), 4.30 (bs, 2H), 3.80 (m, 1H), 2.50 (s, 3H), 2.40 (s, 3H), 1.40 (d, J=7.4 Hz, 6H). Anal. Calc'd for C18H25N5O2S.2.55 CH3OH.1.65HCl: C; 47.77, H; 7.19, N; 13.56. Found: C; 47.84, H; 7.18, N; 13.53.

EXAMPLE IV

Preparation of 3-Amino-4-cyclopropylmethylsulfonyl-6-methyl-1-(2-amino-6-methyl-5-methylenecarboxamidomethylpyridinyl)-2-pyridinone

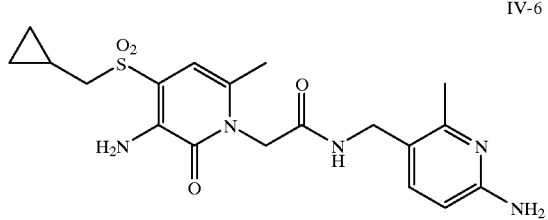

IV-6

Step A: 2-Cyclopropylmethylthiobenzothiazole (IV-1)

A stirred mixture of 2-mercaptobenzothiazole (1.67 g, 10.0 mmol), bromomethylcyclopropane (0.97 mL, 10.0 mmol) and sodium hydrogencarbonate (0.84 g, 10.0 mmol) in absolute ethanol (10 ml) was heated to reflux. After 8 h, the reaction was diluted with ethyl acetate and was washed with water, sodium carbonate solution and brine, dried (Na$_2$SO$_4$) and evaporated in vacuo to give IV-1 as an oil which was used without purification in the next step:

$^1$H NMR (300 Mz, CDCl$_3$) selected signals d 0.39 (m, 2H), 0.65 (m, 2H), 1.26 (m, 1H), 3.32 (d, J=7.3 Hz, 2H).

Step B: 2-Cyclopropylmethylsulfonylbenzothiazole (IV-2)

A solution of potassium permanganate (1.90 g, 12.0 mmol) in water (100 mL) was added to a stirred solution of 2-cyclopropylmethylthiobenzothiazole (1.90 g) in acetic acid (150 mL). After 2 h, the dark brown mixture was decolorized with 10% sodium sulfite solution and water (500 mL) was added. The resulting precipitate was collected by filtration, washing with water, and dried at 0.5 mm Hg, to give IV-2 as a white crystalline solid.

$^1$H NMR (300 Mz, CDCl$_3$) selected signals d 0.28 (m, 2H), 0.64 (m, 2H), 1.21 (m, 1H), 3.46 (d, J=7.3 Hz, 2H).

Step C: 4-Cyclopropylmethylsulfonyl-6-methyl-3-nitro-1-(ethyl-methylenecarboxy)-2-pyridinone (IV-3)

Sodium borohydride (113 mg, 3.0 mmol) was added in portions to a stirred mixture of 2-cyclopropylmethylsulfonylbenzothiazole (0.38 g, 1.50 mmol) in absolute ethanol (3 mL) with cooling. After 2 h, glacial acetic acid was added dropwise to dissolve the suspension, giving a solution pH 4–5 (moist pH paper) and 4-chloro-6-methyl-3-nitro-1-(ethyl-methylenecarboxy)-2-pyridinone (275 mg, 1.0 mmol) was added. The solid quickly dissolves and then a thick precipitate forms. After 2 h the solids were collected by filtration, washing with ethanol, and dried at 0.5 mm Hg to give IV-3 as a bright yellow powder.

$^1$H NMR (CDCl$_3$) d 0.40 (m, 2H), 0.70 (m, 2H), 1.13 (m, 1H), 1.32 (t, J=7.1 Hz, 3H), 2.46 (s, 3H), 3.33 (d, J=7.3 Hz, 2H), 4.28 (q, J=7.1 Hz, 2H), 4.88 (s, 2H), 6.62 (s, 1H)

Step D: 3-Amino-4-cyclopropylmethylsulfonyl-6-methyl-1-(ethyl-methylenecarboxy)-2-pyridinone (IV-4)

A mixture of 4-cyclopropylmethylsulfonyl-6-methyl-3-nitro-1-(ethyl-methylenecarboxy)-2-pyridinone (365 mg) and 10% palladium on carbon (0.30 g) in ethyl acetate (100 mL) was stirred under an atmosphere of hydrogen (balloon) for 3 h. The reaction mixture was filtered through celite, washing with ethyl acetate, and evaporated in vacuo to give IV-4 as a colorless crystalline solid which was used without purification in the next step.

$^1$H NMR (CDCl$_3$) d 0.27 (m, 2H), 0.63 (m, 2H), 1.08 (m, 1H), 1.30 (t, J=7.1 Hz, 3H), 2.23 (d, J=0.9 Hz, 3H), 3.02 (d, J=7.1 Hz, 2H), 4.25 (q, J=7.1 Hz, 2H), 4.80 (s, 2H), 5.88 (br s, 2H), 6.28 (d, J=0.9 Hz, 1H).

Step E: 3-Amino-4-cyclopropylmethylsulfonyl-6-methyl-1-methylenecarboxy-2-pyridinone (IV-5)

Lithium hydroxide hydrate (84 mg, 2.0 mmol) was added to a stirred mixture of 3-amino-4-cyclopropylmethylsulfonyl-6-methyl-1-(ethyl-methylenecarboxy)-2-pyridinone (the product from Step D) in 2:2:1 methanol/THF/water (10 mL). After 2 h a thick white precipitate formed. The mixture was acidified with 1 M HCl to give a clear solution which was partitioned between methylene chloride and brine. The brine was re-extracted with methylene chloride and the combined organic layers were dried (Na2SO4) and evaporated in vacuo to give a crystalline solid. This was heated to reflux as a suspension in methylene chloride (10 mL), cooled and the solids collected by filtration to give IV-5 as a colorless crystalline solid.

$^1$H NMR (d6 DMSO) d 0.25 (m, 2H), 0.50 (m, 2H), 0.92 (m, 1H), 2.20 (s, 3H), 3.18 (d, J=7.1 Hz, 2H), 4.73 (s, 2H), 6.16 (br s, 2H), 6.20 (s, 1H).

Step F: 3-Amino-4-cyclopropylmethylsulfonyl-6-methyl-1-(2-amino-6-methyl-5-methylenecarboxamidomethylpyridinyl)-2-pyridinone (IV-6)

N-Methylmorpholine (0.187 mL, 1.70 mmol) was added to a stirred mixture of 3-amino-4-cyclopropylmethylsulfonyl-6-methyl-1-methylenecarboxy-2-pyridinone (120 mg, 0.40 mmol), 2-amino-5-aminomethyl-6-methylpyrinine dihydrochloride (84 mg, 0.40 mmol), EDC.HCl (96 mg, 0.50 mmol) and HOBT.H2O (68 mg, 0.50 mmol) in DMF (2 mL). After 16 h, water (20 mL) was added to give a white precipitate and after allowing to stand for 30 min, the solids were collected by filtration, washing with water, ethanol and ethyl acetate and air dried. 9.9 M HCl in absolute ethanol (0.1 mL) was added to a stirred fine suspension of the resulting white solid in absolute ethanol (5 mL) to give a solution. Over 1 h a pale yellow crystalline precipitate formed which was collected by filtration, washing with ethanol and dried at 0.5 mm Hg to give IV-6 as a pale peach colored crystalline solid.

$^1$H NMR (d6 DMSO) d 0.25 (m, 2H), 0.50 (m, 2H), 0.91 (m, 1H), 2.17 (s, 3H), 2.44 (s, 3H), 3.17 (d, J=7.1 Hz, 2H), 4.16 (d, J=5.6 Hz, 2H), 4.68 (s, 2H), 6.12 (br s, 2H), 6.18 (d, J=0.7 Hz, 1H), 6.80 (d, J=9.0 Hz, 1H), 7.63 (br s, 2H), 7.76 (d, J=9.0 Hz, 1H), 8.72 (br t, J=5.6 Hz, 1H); Anal. Calc. for C19H25N5O4S.HCl.2H2O: C 46.38, H 6.15, N 14.24. Found: C 46.51, H 6.08, N 13.89.

EXAMPLE V

Preparation of 3-Amino-4-cyclopropylsulfonyl-6-methyl-1-(2-amino-6-methyl-5-methylenecarboxamidomethylpyridinyl)-2-pyridinone

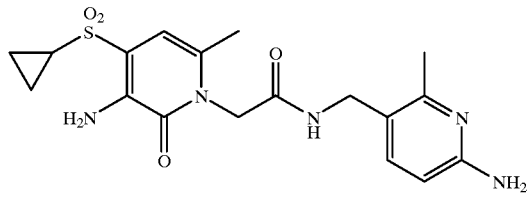

V-3

Step A: Lithium cyclopropylsulfinate (V-1)

V-1 was prepared by a modification of the method of Crowell et. al. (*J. Med. Chem.* 1989, 32, 2436). A solution of cyclopropyl bromide (1.73 mL, 21.6 mmol) in dry diethyl ether (4 mL) was added dropwise to a stirred slurry of 30% lithium dispersion in mineral oil (1.0 g) in dry ether (8 mL) at 0° C. (internal T<5° C.) under nitrogen. After 3 h, an excess of sulfur dioxide was blown on to the surface of the mixture to give a thick white precipitate. The solvent was evaporated in vacuo and absolute ethanol (50 mL) was added cautiously. The resulting mixture was stirred thoroughly and filtered, washing with ethanol. The filtrate was evaporated in vacuo to give V-1 which was used without purification in the next step:

$^1$H NMR (CD3OD) d 0.61 (m, 2H), 0.75 (m, 2H), 1.87 (m, 1H).

Step B: 4-Cyclopropylsulfonyl-6-methyl-3-nitro-1-(ethyl-methylenecarboxy)-2-pyridinone (V-2)

Glacial acetic acid was added dropwise to a solution of the crude lithium cyclopropylsulfinate from Step A (448 mg) in absolute ethanol (2 mL) to give a solution pH 4–5 (moist pH paper). 4-Chloro-6-methyl-3-nitro-1-(ethyl-methylenecarboxy)-2-pyridinone (137 mg, 0.50 mmol) was added to give solution. Over 1 h a thick precipitate forms which was collected by filtration, washing with ethanol, and dried at 0.5 mm Hg to give V-2 as a yellow solid which was used without purification in the next step.

Step C: 3-Amino-4-cyclopropylsulfonyl-6-methyl-1-(2-amino-6-methyl-5-methylenecarboxamidomethylpyridinyl)-2-pyridinone (V-3)

V-3 was prepared from 4-cyclopropylsulfonyl-6-methyl-3-nitro-1-(ethyl-methylenecarboxy)-2-pyridinone using the procedures of Example IV, Steps D–F.

$^1$H NMR (d6 DMSO) d 1.04 (m, 2H), 1.11 (m, 2H), 2.17 (s, 3H), 2.44 (s, 3H), 2.88 (m, 1H), 4.16 (d, J=5.5 Hz, 2H), 4.67 (s, 2H), 6.09 (br s, 2H), 6.18 (d, J=0.6 Hz, 1H), 6.80 (d, J=9.0 Hz, 1H), 7.65 (br s, 2H), 7.77 (d, J=9.0 Hz, 1H), 8.75 (br t, J=5.5 Hz, 1H); Anal. Calc. for C18H23N5O4S.HCl.0.3H2O: C 48.32, H 5.54, N 15.66. Found: C 48.41, H 5.38, N 15.28.

EXAMPLE VI

Preparation of 3-Amino-4-cyclobutylmethylsulfonyl-6-methyl-1-(2-amino-6-methyl-5-methylenecarboxamidomethylpyridinyl)-2-pyridinone

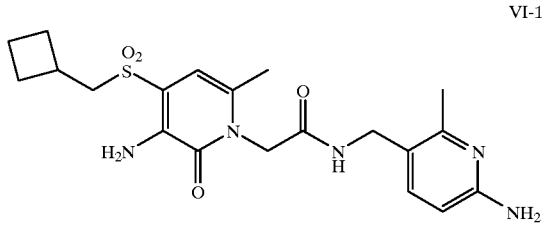

VI-1

VI-1 was prepared from bromomethylcyclobutane using the procedures of Example IV, Steps A–F.

$^1$H NMR (d6 DMSO) d 1.76–2.01 (m, 6H), 2.16 (s, 3H), 2.44 (s, 3H), 2.60 (m, 1H), 3.35 (d, J=7.1 Hz, 2H), 4.16 (d, J=5.1 Hz, 2H), 4.67 (s, 2H), 6.10 (br s, 2H), 6.15 (s, 1H), 6.80 (d, J=9.0 Hz, 1H), 7.66 (br s, 2H), 7.76 (d, J=9.0 Hz, 1H), 8.73 (br t, 1H).

EXAMPLE VII

Preparation of 3-Amino-4-benzylsulfonyl-6-methyl-1-(2-amino-6-methyl-5-methylenecarboxamidomethylpyridinyl)-2-pyridinone

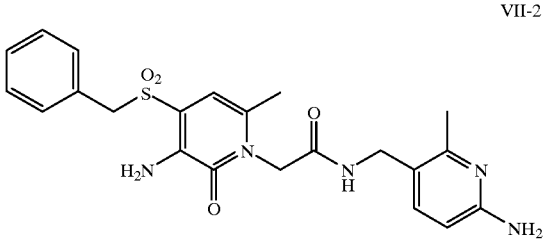

VII-2 a) VII-2 was prepared from benzyl bromide using the procedures of Example IV, Steps A–F.

$^1$H NMR (d6 DMSO) d 2.14 (s, 3H), 2.24 (d, J=1.1 Hz, 3H), 4.12 (d, J=4.8 Hz, 2H), 4.54 (s, 2H), 4.67 (s, 2H), 5.72 (s, 2H), 6.05 (br s, 3H), 6.23 (d, J=8.2 Hz, 1H), 7.21 (d, J=8.2 Hz, 1H), 7.27–7.34 (m, 5H), 8.43 (br t, 1H).

b) Alternatively, VII-2 may be prepared from 4-benzylthio-6-methyl-3-nitro-1-(ethyl-methylenecarboxy)-2-pyridinone by oxidation with OXONE® to give 4-benzylsulfonyl-6-methyl-3-nitro-1-(ethyl-methylenecarboxy)-2-pyridinone (VII-1), followed by the use of the procedures of Example IV, Steps D–F:

Preparation of 4-Benzylsulfonyl-6-methyl-3-nitro-1-(ethyl-methylenecarboxy)-2-pyridinone (VII-1)

A mixture of 4-benzylthio-6-methyl-3-nitro-1-(ethyl-methylenecarboxy)-2-pyridinone (135 mg, 0.373 mmol) and OXONE® (688 mg, 1.12 mmol) in 1:1 methanol/water (3 mL) was stirred for 9 days. The mixture was partitioned between ethyl acetate and water and the organic layer was washed with 5% sodium metabisulfite solution and brine, dried (Na2SO4) and evaporated in vacuo to an oil. The crude product was purified by flash column chromatography on silica (70% ethyl acetate/hexanes) to give VII-1.

1H NMR (CDCl3) d 1.32 (t, J=7.1 Hz, 3H), 2.24 (s, 3H), 4.27 (q, J=7.1 Hz, 2H), 4.62 (s, 2H), 4.81 (s, 2H), 6.00 (s, 1H), 7.36 (s, 5H).

EXAMPLE VIII

Preparation of 3-Amino-4-phenylsulfonyl-6-methyl-1-(2-amino-6-methyl-5-methylenecarboxamidomethylpyridinyl)-2-pyridinone

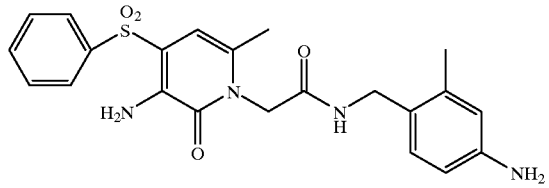

VIII-2

Step A: 6-Methyl-3-nitro-4-phenylsulfonyl-1-(ethyl-methylenecarboxy)-2-pyridinone (VIII-1)

4-Chloro-6-methyl-3-nitro-1-(ethyl-methylenecarboxy)-2-pyridinone (100 mg, 0.40 mmol) was added to a stirred solution of sodium benzene sulfinate (66 mg, 0.40 mmol) in DMF (0.40 ml). After 2 h the mixture was partitioned between water and ethyl acetate. The organic layer was dried (Na2SO4) and evaporated in vacuo to a yellow gum which was purified by flash column chromatography (ethyl acetate/hexanes gradient, 40–70% ethyl acetate) to give VIII-1 as a yellow gum.

$^1$H NMR (CD3OD) d 1.26 (t, J=7.1 Hz, 3H), 2.46 (s, 3H), 4.22 (q, J=7.1 Hz, 2H), 4.90 (s, 2H), 6.80 (s, 1H), 7.66–8.05 (m, 5H).

Step B: 3-Amino-4-phenylsulfonyl-6-methyl-1-(2-amino-6-methyl-5-methylenecarboxamidomethylpyridinyl)-2-pyridinone (VIII-2)

VIII-2 was prepared, as the free base, from 6-methyl-3-nitro-4-phenylsulfonyl-1-(ethyl-methylenecarboxy)-2-pyridinone using the procedures of Example IV, Steps D–F.

$^1$H NMR (d6 DMSO) d 2.15 (s, 3H), 2.42 (s, 3H), 4.13 (d, J=5.7 Hz, 2H), 4.62 (s, 2H), 6.29 (s, 1H), 6.32 (s, 2H), 6.79 (d, J=9.0 Hz, 1H), 7.24 (t, J=4.4 Hz, 1H), 7.67 (br s, 2H), 7.74 (d, J=9.0 Hz, 1H), 7.94 (dd, J=0.6 and 3.7 Hz, 1H), 8.07 (dd, J=0.6 and 4.9 Hz, 1H), 8.41 (br t, 1H).

EXAMPLE IX

Preparation of 3-Amino-4-(2-thienylsulfonyl)-6-methyl-1-(2-amino-6-methyl-5-methylenecarboxamidomethylpyridinyl)-2-pyridinone

IX-1

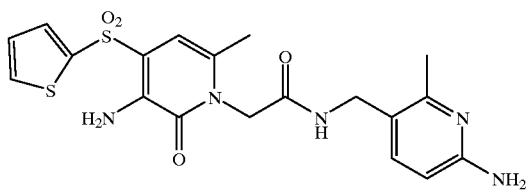

IX-1 was prepared as the HCl salt from 4-chloro-6-methyl-3-nitro-1-(ethyl-methylenecarboxy)-2-pyridinone and sodium thienylsufinate [which was prepared by the method of Crowell et. al. (*J. Med. Chem.* 1989, 32, 2436)] using the procedure of Example VIII.

$^1$H NMR (d6 DMSO) d 2.14 (s, 3H), 2.20 (s, 3H), 4.08 (d, J=4.9 Hz, 2H), 4.60 (s, 2H), 5.70 (s, 2H), 6.21 (d, J=8.2 Hz, 1H), 6.29 (s, 1H), 6.30 (s, 2H), 7.17 (d, J=8.2 Hz, 1H), 7.62–7.99 (m, 5H), 8.41 (br t, 1H).

EXAMPLE X

Preparation of 3-Amino-4-benzylthio-6-methyl-1-(2-amino-6-methyl-5-methylenecarboxamidomethylpyridinyl)-2-pyridinone

X-2

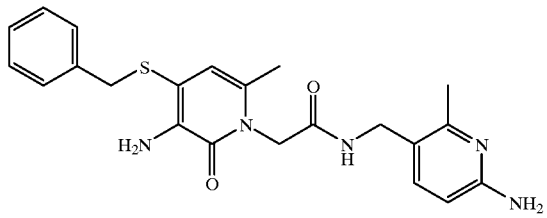

Step A: 3-Amino-4-benzylthio-6-methyl-1-(ethyl-methylenecarboxy)-2-pyridinone (X-1)

Iron powder (39 mg) was added to a stirred solution of 4-benzylthio-6-methyl-3-nitro-1-(ethyl-methylenecarboxy)-2-pyridinone [prepared from benzyl mercaptan and 4-chloro-6-methyl-3-nitro-1-(ethyl-methylenecarboxy)-2-pyridinone using the procedure of Example III, Step B] in a mixture of acetic acid (1.1 mL) and water (0.2 mL) and the resulting mixture was heated to 90° C. After 4 h, the mixture was cooled and filtered, washing with acetic acid. The filtrate was partitioned between ethyl acetate and water and the organic layer was washed with water, dried (Na2SO4) and evaporated in vacuo to an oil. The crude product was purified by flash column chromatography on silica (30% ethyl acetate/hexanes) to give X-1 as an oil.

1H NMR (CDCl3) d 1.28 (t, J=7.3 Hz, 3H), 2.16 (s, 3H), 4.00 (s, 2H), 4.24 (q, J=7.3 Hz, 2H), 4.46 (br s, 2H), 4.78 (s, 2H), 5.98 (s, 1H), 7.26 (m, 5H).

Step B: 3-Amino-4-benzylthio-6-methyl-1-(2-amino-6-methyl-5-methylenecarboxamidomethylpyridinyl)-2-pyridinone (X-2)

X-2 was prepared, as the free base, from 3-amino-4-benzylthio-6-methyl-1-(ethyl-methylenecarboxy)-2-pyridinone using the procedures of Example IV, Steps E and F.

MS (FAB) 424 (M+1)+.

EXAMPLE XI

Preparation of 3-Carboxymethylamino-4-cyclohexylmethyl-6-methyl-1-(2-amino-6-methyl-5-methylenecarboxamidomethylpyridinyl)-2-pyridinone

XI-7

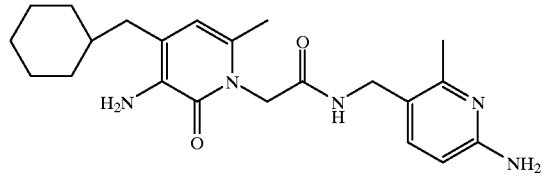

Step A: 1-(t-Butyl methylenecarboxy)-6-Methyl-3-nitro-pyridin[1H]-2-one (XI-1)

To a 0° C. stirred suspension of 1.0 g (6.49 mmol) of 6-methyl-3-nitropyridin-2-one in 15 mL anhydrous DMF under Ar was added 262 mg (6.55 mmol) of NaH (60% in mineral oil) in 3 portions. After the mixture became homogeneous over 15 min, 1.06 mL (6.55 mmol) of t-butyl bromoacetate was in two portions. The cold bath was removed and the reaction mixture stirred under Ar overnight. An additional portion of 0.2 mL of t-butyl bromoacetate was added, and the reaction heated to 50° C. for 17 h. Concentration of the reaction mixture at reduced pressure gave a residue that was partitioned between ethyl acetate and 1M citric acid. The aq. layer was extracted with ethyl acetate, and the combined organic layers washed with 10% Na$_2$CO$_3$, brine, treated with activated carbon, dried over Na$_2$SO$_4$, and the solvents removed to give an oil that was chromatographed on 12 g of SiO$_2$ using 1:2 to 1:1 EtOAc-hexanes which gave XI-1 as a yellow solid:

$^1$H NMR (CDCl$_3$) ∂ 8.34 (d, 1H, 8.0 Hz), 6.20 (d, 1H, 7.8 Hz), 4.81 (s, 2H), 2.43 (s, 3H), 1.49 (s, 9H).

Step B: 1-(t-Butyl methylenecarboxy)-4-cyclohexylmethyl-3,4-dihydro-6-methyl-3-nitro-pyridin[1H]-2-one (XI-2)

To a stirred suspension of 73 mg (3.0 mmol) of Mg turnings and a small crystal of 12 in 3 mL of dry THF was added 349 μL (2.5 mmol) of bromomethylcyclohexane, and the mixture heated to reflux for 2 h as the Mg slowly dissolved. After cooling to ambient temperature, the resulting solution was added dropwise via syringe to a −78° C. stirred solution of 537 mg (2.0 mmol) 1-(t-butyl methylenecarboxy)-6-methyl-3-nitro-pyridin[1H]-2-one in 6 mL of dry THF. After stirring in the cold for 45 min, the cold bath was removed and, as the reaction reached −15° C., it was quenched by the dropwise addition of 286 μL (5 mmol) of acetic acid. After removal of the solvents at reduced pressure, the residue was partitioned between EtOAc and cold 5% HCl. The organic layer was washed with 5% NaHCO$_3$, brine, dried over Na$_2$SO$_4$ and the solvents removed to give a yellow oil that was chromatographed on 50 g of SiO$_2$ using 1:3 EtOAc-hexane to give XI-2 as a yellow semi-solid:

$^1$H NMR (CDCl$_3$) ∂ 4.97–5.0 (m, 2H), 4.42 (d, 1H, 17.6 Hz), 4.21 (d, 2H, 17.7 Hz), 3.25–3.35 (m, 1H), 1.89 (t, 3H, 1.5 Hz), 1.60–1.80 (m, 6H), 1.49 (s, 9H), 1.03–1.48 (m, 11 H), 0.8–1.02 (m, 2H).

Step C: 1-(t-Butyl methylenecarboxy)-4-cyclohexylmethyl-6-methyl-3-nitro-pyridin[1H]-2-one (XI-3)

To a stirred suspension of 104 mg of nickel peroxide hydrate in 5 mL of CHCl$_3$ was added 126 mg (0.34 mmol) of 1-(t-butyl methylenecarboxy)-4-cyclohexylmethyl-3,4-dihydro-6-methyl-3-nitro-pyridin[1H]-2-one. After 2 h, an additional 127 mg of nickel peroxide hydrate was added, and the mixture stirred for another 2 h. Filtration and concentration of the filtrate at reduced pressure gave XI-3 as a yellow oil:

$^1$H NMR (CDCl$_3$) ∂ 5.95 (s, 1H), 4.74 (s, 2H), 2.37 (d, 1H, 7.1 Hz), 2.31 (s, 3H), 1.52–1.80 (m, 6H), 1.48 (s, 9H), 1.03–1.30 (m, 8 H), 0.85–1.02 (m, 3H).

Step D: 1-Methylenecarboxy-4-cyclohexylmethyl-6-methyl-3-nitro-pyridin[1H]-2-one (XI-4)

To a stirred solution of 120 mg (0.33 mmol) of 1-(t-butyl methylenecarboxy)-4-cyclohexylmethyl-6-methyl-3-nitro-pyridin[1H]-2-one in 7.5 mL of CH2Cl2 was added 7.5 mL of TFA and stirred under Ar for 1 h. The solvents were removed at reduced pressure, and the residue partitioned between EtOAc and water. The aqueous layer was extracted with EtOAc and the combined organic layers washed with brine, treated with activated carbon, dried over Na$_2$SO$_4$ and solvents removed to give XI-4 as a light tan solid which was carried forward to the next step.

Step E: 4-Cyclohexylmethyl-6-methyl-3-nitro-1-(2-t-butyloxycarbonylamino-6-methyl-5-methylenecarboxamidomethylpyridinyl)-pyridin[1H]-2-one (XI-5)

The product from Step C was dissolved in 3 mL of DMF along with 44 mg (0.32 mmol) of 1-hydroxybenzotriazole and 77 mg (0.32 mmol) of 2-t-butyloxycarbonylamino-5-aminomethyl-6-methylpyridine. To this stirred solution was added 62 mg (0.32 mmol) of EDC and 90 μL (0.65 mmol) of triethylamine, and stirred under Ar overnight. The solvents were removed at reduced pressure, and the residue partitioned between EtOAc and 1M citric acid. The aqueous layer was extracted with EtOAc, and the combined organic layers washed with 10% Na$_2$CO$_3$, brine, treated with activated carbon, dried over Na$_2$SO$_4$ and the solvents removed at reduced pressure to give XI-5 as a yellow oil which was carried forward to the next step.

Step F: 3-Amino-4-cyclohexylmethyl-6-methyl-1-(2-t-butyloxycarbonylamino-6-methyl-5-methylenecarboxamidomethylpyridinyl)-pyridin[1H]-2-one (XI-6)

The product from Step D was dissolved in 18 mL of ethanol, 2 mL of water, 1 mL of acetic acid and hydrogenated at 50 psi using 32 mg of 20% Pd(OH)$_2$ on carbon overnight. The catalyst was removed by filtration, concentrated at reduced pressure and the residue partitioned between CHCl3 and 10% Na$_2$CO$_3$. The organic layer was dried over Na2SO4 and the solvents removed at reduced pressure to give XI-6 as a yellow oil:

$^1$H NMR (CDCl$_3$) ∂ 7.64 (d, 1H, 8.3 Hz), 7.38 (d, 1H, 8.4 Hz), 7.36 (br t, 1H), 7.12 (br s, 1H), 5.88 (s, 1H), 4.73 (s, 2H), 4.33 (d, 2H, 5.7 Hz), 3.93 (s, 2H), 2.37 (s, 3H), 2.34 (s, 3H), 2.24 (d, 7.1 Hz), 1.51–1.75 (m, 7H), 1.50 (s, 9H), 1.05–1.28 (m, 4H), 0.92–1.05 (m, 2H).

Step G: 3-Amino-4-cyclohexylmethyl-6-methyl-1-(2-amino-6-methyl-5-methylenecarboxamidomethylpyridinyl)-2-pyridinone (XI-7)

The product from Step F was dissolved in 5 mL of CH2Cl2 and treated with 5 mL of TFA under Ar for 1 h, concentrated at reduced pressure and purified by gradient elution preparative HPLC using a C-18 stationary phase and 0.1% aqueous TFA/CH$_3$CN as the mobile phase. The fractions were assayed by analytical HPLC, combined and concentrated at reduced pressure and lyophilized to provide XI-7 as a colorless solid:

$^1$H NMR (D$_6$-DMSO) ∂ 8.68 (br t, 1H), 7.78 (d, 1H, 9.1 Hz), 7.74 (br s, 2H), 6.80 (d, 1H, 8.8 Hz), 5.91 (s, 1H), 4.66 (s, 2H), 4.15 (br d, 2H), 2.43 (s, 3H), 2.20–2.40 (m, 5 H), 2.16 (s, 3H), 1.50–1.70 (m, 6 H), 1.05–1.25 (m, 3H), 0.9–1.05 (m, 2H).

EXAMPLE XII

Tablet Preparation

Tablets containing 10.0, 25.0, and 50.0 mg, respectively, of compound VII-2 are prepared as illustrated below:

| Ingredient | Amount-mg | | |
|---|---|---|---|
| VII-2 | 10.0 | 25.0 | 50.0 |
| Microcrystalline cellulose | 80.0 | 100.0 | 150.0 |
| Modified food corn starch | 10.0 | 15.0 | 20.0 |
| Magnesium stearate | 0.75 | 1.0 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 10.0, 25.0, and 50.0 mg, respectively, of active ingredient per tablet.

EXAMPLE XIII

An intravenous dosage form of the above-indicated active compound is prepared as follows:

| | |
|---|---|
| VII-2 | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the following structure:

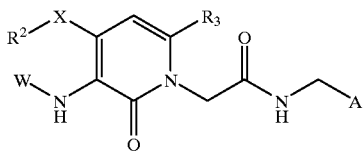

wherein
W is
hydrogen,
$R^1$—,
$R^1OC(O)$—,
$R^1C(O)$—,
$R^1SO_2$—,
$(R^1)_m(CH_2)_nNH_qC(O)$—,
   where n is 0–4, m is 1 or 2, wherein $R^1$ is same or different, and q is 0 or 1, with the proviso that where n is 1–4, q is 1 and m is 1, and where n is 0, m is 1 or 2, and q is 0 or 1, and where n is 0, m is 2 and q is 0;

$R^1$ is
$R^{17}(CH_2)_t$—, where t is 0–4;
$(R^{17})(OR^{17})CH(CH_2)_p$—, where p is 1–4,
$(R^{17})_2CH(CH_2)_r$—, where r is 0–4 and each $R^{17}$ can be the same or different, and wherein $(R^{17})_2$ can also form a ring with CH represented by $C_{3-7}$ cycloalkyl, $C_{7-12}$ bicylic alkyl, $C_{10-16}$ tricylic alkyl, or a 5- to 7- membered mono- or bicyclic heterocyclic ring which can be saturated or unsaturated, and which contains from one to three heteroatoms selected from the group consisting of N, O and S,
$R^{17}O(CH_2)_p$—, wherein p is 1–4;

$R^2$, $R^{14}$ and $R^{17}$ are independently selected from
-phenyl, unsubstituted or substituted with one or more of
   $C_{1-4}$ alkyl,
   $C_{1-4}$ alkoxy,
   halogen,
   hydroxy,
   COOH, or
   $CONH_2$,
naphthyl,
biphenyl,
a 5- to 7-membered mono- or a 9- to 10-membered bicyclic heterocyclic ring which can be saturated or unsaturated, and which contains from one to four heteroatoms selected from the group consisting of N, O and S,
—$C_{1-7}$ alkyl, unsubstituted or substituted with one or more of hydroxy,
   COOH,
   amino,
   aryl,
   $C_{3-7}$ cycloalkyl,
   heteroaryl, or
   heterocycloalkyl,
—$CF_3$
$C_{3-7}$ cycloalkyl,
$C_{7-12}$ bicyclic alkyl, or
$C_{10-16}$ tricyclic alkyl;

X is
$CF_2$,
$CR^{15}$, $R^{16}$
   wherein $R^{15}$ and $R^{16}$ are independently hydrogen,
   $C_{3-7}$ cycloalkyl,
   $C_{1-4}$ alkyl unsubstituted or substituted with one or more of hydroxy,
      COOH,
      amino,
      aryl,
      heteroaryl, or
      heterocycloalkyl,
   aryl,
   heteroaryl,
   heterocycloalkyl, or
   $R^{15}$ and $R^{16}$ are joined to form a four to seven membered cycloalkyl ring unsubstituted or substituted with hydroxy, amino or aryl, or
$S(O)_r$, where r is 0–2;

$R^3$ is
hydrogen,
$C_{1-4}$ alkyl,
$C_{3-7}$ cycloalkyl, or
trifluoromethyl;

A is chosen from one of the following radicals:

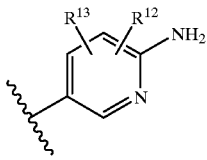

II

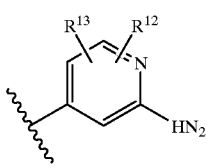

III

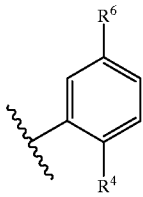

IV with the proviso that when A is radical IV, $R^2$—X is not $C_{1-4}$ alkyl, $C_{3-7}$ cycloalkyl, or trifluoromethyl;

$R^4$ is
hydrogen,
$C_{1-4}$ alkyl,
$C_{1-4}$ alkoxy,
halogen,
—$OCH_2CF_3$,
—COOH,
—OH,
—$COOR^6$, where $R^6$ is $C_{1-4}$alkyl,
—$CONR^7R^8$, where $R^7$ and $R^8$ are independently hydrogen or $C_{1-4}$alkyl,
—$(CH_2)_{1-4}OH$, —CH$_2$NHC(O)CH$_3$,
—CH$_2$NHC(O)CF$_3$,
—CH$_2$NHSO$_2$CH$_3$,
—SO$_2$NH$_2$,
—(CH$_2$)$_{1-4}$SO$_2$NR$^7$R$^8$,
—(CH$_2$)$_{1-4}$SO$_2$R$^6$,
a 5- to 7-membered mono- or a 9- to 10-membered bicyclic heterocyclic ring which can be saturated or unsaturated, and which contains from one to four heteroatoms selected from the group consisting of N, O and S,
—ZCH$_2$CO$_2$H,
—ZCH$_2$CO$_2$CH$_3$,
—ZCH$_2$R$^{14}$,
—ZCH$_2$CO$_2$(CH$_2$)$_{1-3}$CH$_3$,
—Z(CHR$^9$)$_{1-3}$C(O)NR$^{10}$R$^{11}$,
wherein
R$^9$ is H or C$_{1-4}$ alkyl,
R$^{10}$ and R$^{11}$ are independently
hydrogen,
C$_{3-7}$ cycloalkyl,
aryl,
heteroaryl,
heterocycloalkyl,
C$_{1-4}$ alkyl unsubstituted or substituted with one or more of hydroxy,
COOH,
amino,
aryl,
heteroaryl, or
heterocycloalkyl, or
R$^{10}$ and R$^{11}$ are joined to form a four to seven membered cycloalkyl ring unsubstituted or substituted with hydroxy, amino or aryl,
wherein Z is O, S or CH$_2$;
R$^5$ is
hydrogen,
halogen,
C$_{1-4}$ alkyl,
C$_{1-4}$ alkoxy,
CN, or
CO$_2$NH$_2$; and
R$^{12}$ and R$^{13}$ are independently
hydrogen,
C$_{1-4}$ linear or branched alkyl or alkoxy,
C$_{3-7}$ cycloalkyl,
halogen, or
trifluoromethyl;
and pharmaceutically acceptable salts thereof.

2. The compound of claim 1 having the formula:

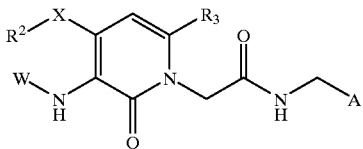

wherein
W is
hydrogen,
—C$_{1-4}$ alkyl,
—C$_{3-7}$cycloalkyl,
—SO$_2$C$_{1-7}$ alkyl, or
—(CH$_2$)$_n$COOH, where n is 1–4;
R$^2$ is
—C$_{1-7}$ alkyl
—(CH$_2$)$_u$—C$_{3-7}$cycloalkyl, wherein u is 0, 1, or 2,
—(CH$_2$)$_u$-phenyl, wherein phenyl is unsubstituted or substituted with one or more of the moieties selected from the group consisting of
C$_{1-4}$ alkyl,
C$_{1-4}$ alkoxy,
halogen,
hydroxy,
COOH, or
CONH$_2$
wherein u is 0, 1, or 2,
-2-thienyl, or
-3-thienyl;
X is
—S—, —SO$_2$—, or CH$_2$;
R$^3$ is
C$_{1-4}$ linear alkyl;
A is chosen from one of the following radicals:

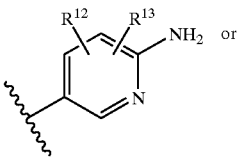

II

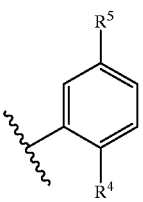

IV with the proviso that when A is radical IV, R$^2$—X— is not C$_{1-4}$ alkyl, and pharmaceutically acceptable salts thereof.

3. The compound of claim 2 having the formula:

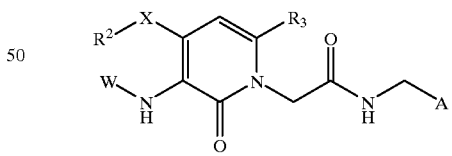

wherein
W is
hydrogen,
—SO$_2$CH$_3$, or
—CH$_3$,
—CH$_2$COOH;
R$^2$ is
—CH$_3$,
—(CH$_2$)$_u$—C$_{3-6}$cycloalkyl, wherein u is 0 or 1;
—(CH$_2$)$_u$-phenyl, wherein u is 0 or 1,
—CH$_2$C(CH$_3$)$_3$, —CH(CH$_3$)$_2$,
-phenyl-CH$_3$,
-2-thienyl, or
-3-thienyl;
X is
—S—, —SO$_2$—, or CH$_2$;
R$^3$ is
—CH$_3$;
A is chosen from one of the following radicals:
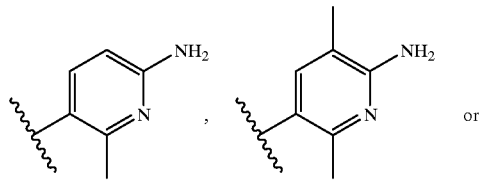
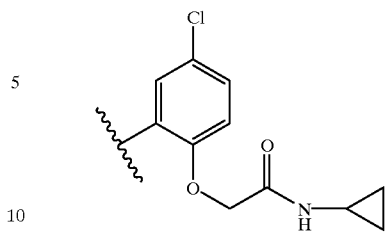
IV
with the proviso that when A is radical IV, R$^2$—X— is not C$_{1-4}$ alkyl, and pharmaceutically acceptable salts thereof.
4. The compound of claim 3 selected from the group consisting of:
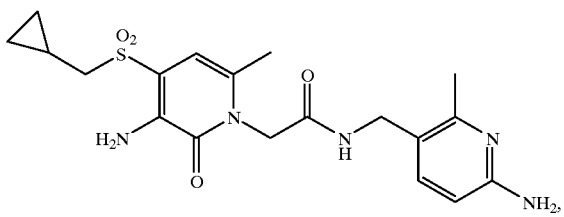
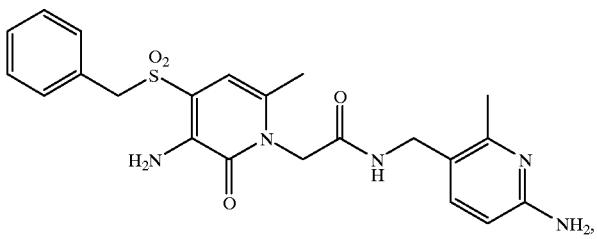
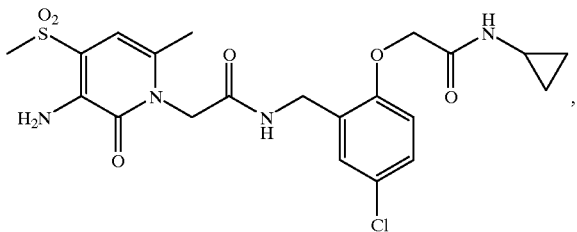
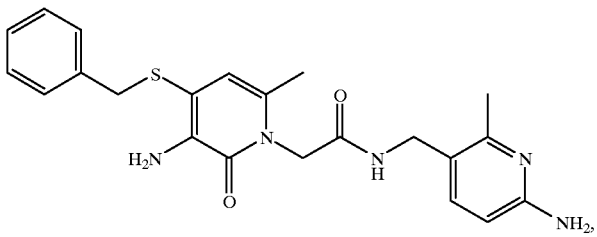

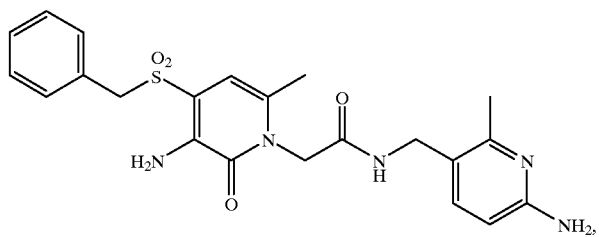
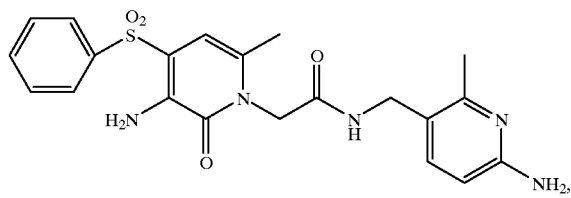
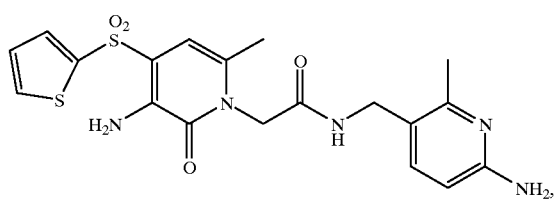
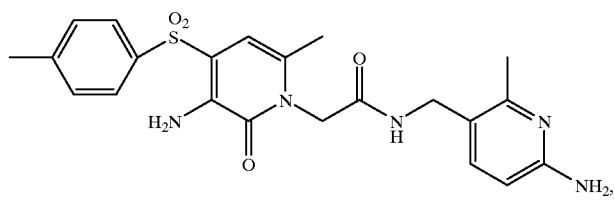
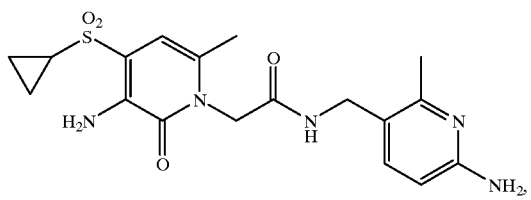
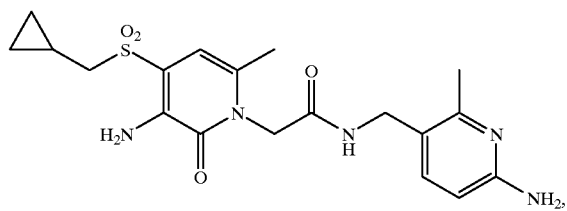
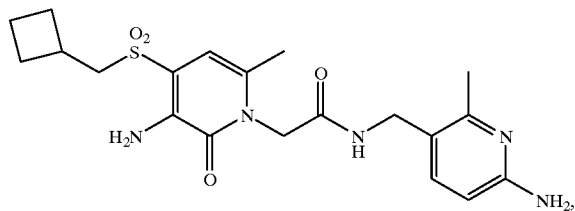

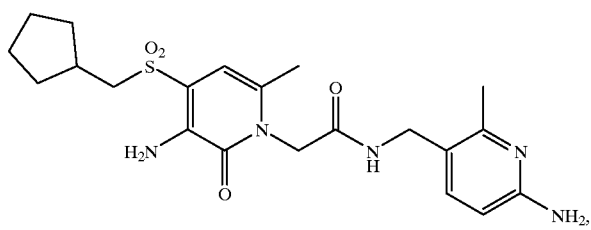
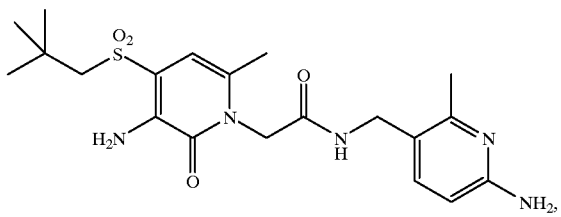
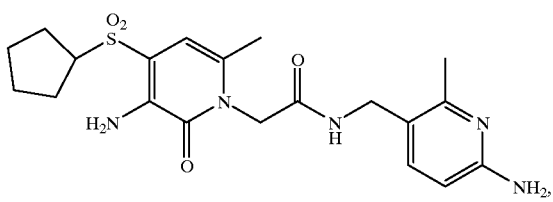
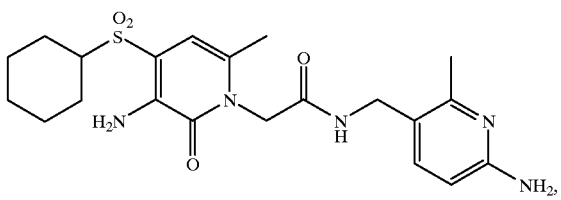
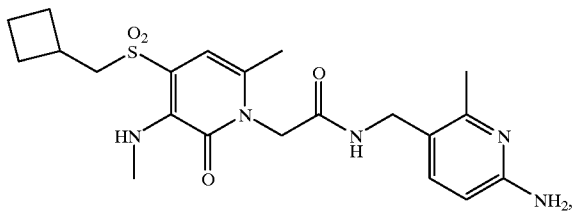
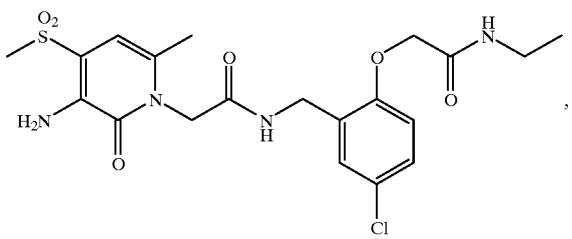
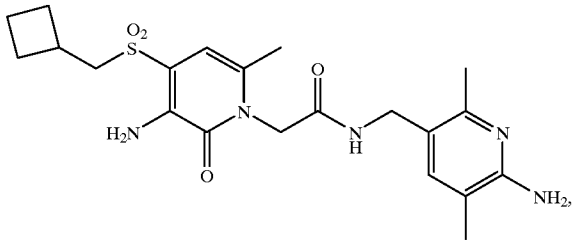

-continued

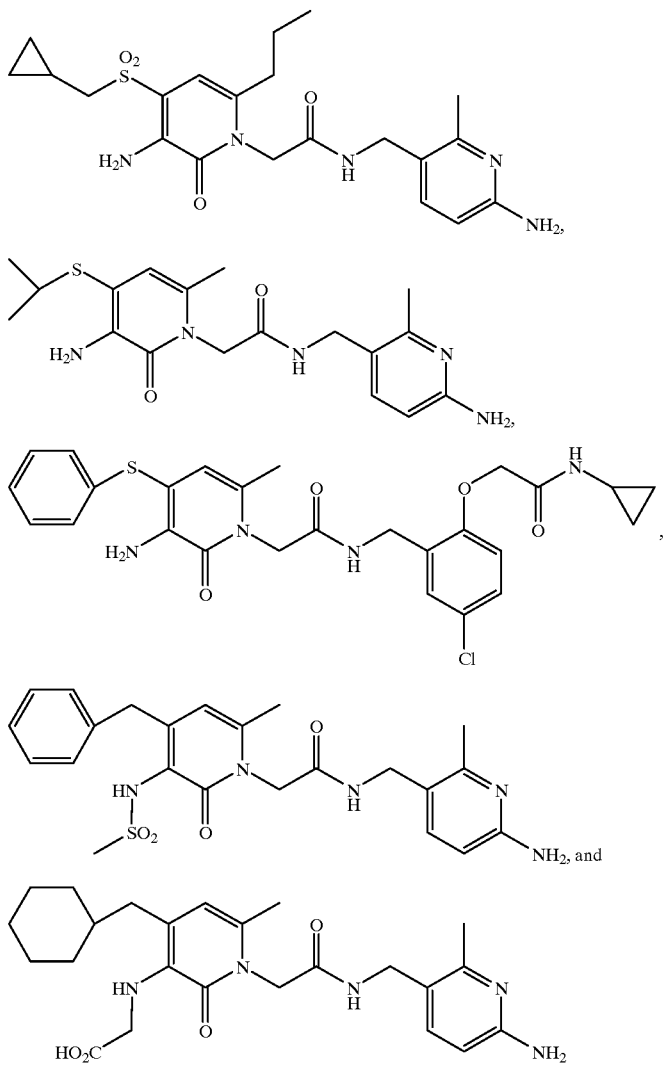

and pharmaceutically acceptable salts thereof.

5. A composition for inhibiting thrombin in blood comprising a compound of claim 1 and a pharmaceutically acceptable carrier.

6. A method for inhibiting thrombin in blood in a mammal comprising administering to the mammal a composition of claim 5.

7. A method for inhibiting formation of blood platelet aggregates in blood in a mammal comprising administering to the mammal a composition of claim 5.

8. A method for inhibiting formation of fibrin in blood in a mammal comprising administering to the mammal a composition of claim 5.

9. A method for inhibiting thrombus formation in blood in a mammal comprising administering to the mammal a composition of claim 5.

10. A method for inhibiting thrombin in stored blood comprising administering to the mammal a composition of claim 5.

11. A method for treating atrial fibrillation, deep venous thrombosis, pulmonary embolism, cardiac thromoembolism and associated stroke in patients with atrial fibrillation, mechanical heart valves, or recent myocardial infarction with decreased left ventricular function in a mammal comprising administering to the mammal a composition of claim 5.

12. A method for preventing atrial fibrillation, deep venous thrombosis, pulmonary embolism, cardiac thromoembolism and associated stroke in patients with atrial fibrillation, mechanical heart valves, or recent myocardial infarction with decreased left ventricular function in a mammal comprising administering to the mammal a composition of claim 5.

* * * * *